(12) United States Patent
Hernandez

(10) Patent No.: US 12,016,939 B2
(45) Date of Patent: Jun. 25, 2024

(54) SKIN TREATMENT METHODS AND COMPOSITIONS FOR TRANSDERMAL DELIVERY OF ACTIVE AGENTS

(71) Applicant: Topix Pharmaceuticals, Inc., North Amityville, NY (US)

(72) Inventor: Steven M. Hernandez, Blue Point, NY (US)

(73) Assignee: Topix Pharmaceuticals, Inc., North Amityville, NY (US)

( * ) Notice: Subject to any disclaimer, the term of this patent is extended or adjusted under 35 U.S.C. 154(b) by 0 days.

(21) Appl. No.: 18/112,635

(22) Filed: Feb. 22, 2023

(65) Prior Publication Data

US 2023/0190593 A1    Jun. 22, 2023

Related U.S. Application Data

(62) Division of application No. 17/144,691, filed on Jan. 8, 2021, now Pat. No. 11,596,584.

(60) Provisional application No. 62/959,874, filed on Jan. 10, 2020.

(51) Int. Cl.
| | |
|---|---|
| A61K 8/06 | (2006.01) |
| A61K 8/34 | (2006.01) |
| A61K 8/39 | (2006.01) |
| A61K 8/49 | (2006.01) |
| A61K 8/67 | (2006.01) |
| A61Q 19/08 | (2006.01) |

(52) U.S. Cl.
CPC ............. *A61K 8/068* (2013.01); *A61K 8/34* (2013.01); *A61K 8/345* (2013.01); *A61K 8/347* (2013.01); *A61K 8/39* (2013.01); *A61K 8/4973* (2013.01); *A61K 8/671* (2013.01); *A61Q 19/08* (2013.01); *A61K 2800/5422* (2013.01); *A61K 2800/805* (2013.01)

(58) Field of Classification Search
None
See application file for complete search history.

(56) References Cited

U.S. PATENT DOCUMENTS

| | | |
|---|---|---|
| 8,034,755 B2 | 10/2011 | Kawano |
| 9,364,406 B2 | 6/2016 | Vince et al. |
| 9,403,778 B2 | 8/2016 | Vince et al. |

(Continued)

FOREIGN PATENT DOCUMENTS

| | | |
|---|---|---|
| EP | 0487404 A1 | 5/1992 |
| EP | 1093796 A1 | 4/2001 |

(Continued)

OTHER PUBLICATIONS

European Search Report for EP Patent Application No. 21703347.1 dated Sep. 29, 2022, 5 pages.
Database GNPD [Online] Mintel; Jun. 11, 2019 (Jun. 11, 2019) anonymous: "Instant Sunless Lotion" XP055950649, Database accession No. 6609687, 4 pages.
Database GNPD [Online] Mintel; Oct. 11, 2011 (Oct. 11, 2011), anonymous: "Self-Tanning Bronzer Mousse", KP055950650, Database accession No. 1639160, 2 pages.

(Continued)

*Primary Examiner* — Kyung S Chang
(74) *Attorney, Agent, or Firm* — LOWENSTEIN SANDLER LLP

(57) ABSTRACT

Disclosed are stable, non-irritating, skin treatment active agents containing formulations and delivery systems for topical application to the skin. The disclosed topical formulations and delivery systems provide controlled, gentle release of the active agents into the skin for the treatment of amenable skin conditions as well as for improvement of aesthetic skin properties. Also provided are methods for the formulation, manufacture and use of the disclosed formulations and delivery systems.

9 Claims, 4 Drawing Sheets

(56) References Cited

U.S. PATENT DOCUMENTS

| | | |
|---|---|---|
| 9,795,545 B2 | 10/2017 | Fassih |
| 9,987,211 B2 | 6/2018 | Vince et al. |
| 10,383,942 B2 | 8/2019 | Oefelein |
| 2004/0115159 A1 | 6/2004 | Tadlock |
| 2006/0177398 A1 | 8/2006 | McCook |
| 2006/0204526 A1 | 9/2006 | Lathrop |
| 2011/0117036 A1 | 5/2011 | Chaudhuri |
| 2012/0128602 A1 | 5/2012 | Dobos et al. |
| 2013/0018104 A1 | 1/2013 | Lathrop |
| 2015/0272896 A1 | 10/2015 | Sun |
| 2018/0243196 A1 | 8/2018 | Shaffer et al. |
| 2018/0271760 A1 | 9/2018 | Baca |

FOREIGN PATENT DOCUMENTS

| | | |
|---|---|---|
| WO | 9304665 A1 | 3/1993 |
| WO | 2011050102 A1 | 4/2011 |
| WO | 2014187950 A1 | 11/2014 |
| WO | 2015187921 A1 | 12/2015 |

OTHER PUBLICATIONS

International Preliminary Report on Patentability for PCT/US2021/012679 dated Jul. 12, 2022, 7 pages.

International Search Report and Written Opinion for PCT/US21/12679 dated May 13, 2021, 14 pages.

Draelos et al., "A Double-Blind, Comparative Clinical Study for Newly Formulated Retinol Serums vs. Tretinoin Cream In Escalating Doses: A Method for Rapid Retinization with Minimized Imitation", Journal of Drugs in Dermatology, vol. 19. Issue 6, Jun. 2020, 7 pages.

Chinese Office Action for CN Patent Application No. 202180000188.8, dated Dec. 28, 2023, 11 pages, with translation, 14 pages.

Histology. New collagen formation in retinol treated subject from baseline (6A H&E 100x, 6C H&E 200x) to Week 12 (6B H&E 100x, 6D H&E 200x).

SKIN TREATMENT METHODS AND COMPOSITIONS FOR TRANSDERMAL DELIVERY OF ACTIVE AGENTS

RELATED APPLICATIONS

The present application is a divisional application of U.S. application Ser. No. 17/144,691, filed on Jan. 8, 2021, which claims priority to U.S. Provisional Patent Application No. 62/959,874, filed on Jan. 10, 2020, which are herein incorporated by reference in their entirety.

FIELD

The present invention relates to the field of dermatological compositions and methods for skin treatments having at least one retinoid and/or other active agents and delivery systems thereof for transdermal delivery. Certain disclosed embodiments provide effective, gentle activation solvent systems, including dermatological compositions and methods having retinol and activation and delivery systems thereof, for topical application to the skin, as well as to methods for their formulation, manufacture and use thereof.

BACKGROUND

Active agents are used in skin treatments of various and diverse dermatological conditions such as psoriasis, photoaging, age spots, aged appearance of the skin due to extrinsic and intrinsic causes, skin wrinkles, acne, hyperpigmentation and skin cancers. Active agents typically are prescription active agents and non-prescription active agents. Solvents used in dermatological formulations having skin treatment active agents may be strong solvents, such as acetone, or mild, i.e., gentle, solvents. However, strong solvents are known to cause skin condition effects that require additional treatment including disruption of the skin barrier, and may interfere with patients' compliance with skin treatment regimens. Mild solvents, on the other hand, are known to be ineffective in delivery of active agents in transdermal and cutaneous uses. Furthermore, with present tendency toward extended use of dermatological formulations in skincare, there is a continued need for topical formulations of active agents for various skin treatments.

Retinoids are useful in the treatment of various and diverse dermatological conditions, including inflammatory disorders, conditions characterized by increased cell turnover such as psoriasis, photoaging, age spots, skin wrinkles, enlarged pores, oily skin, skin appearing prematurely aged, acne, and skin cancers.

However, retinoids, particularly retinol, are unstable and easily oxidized in the presence of air as well as in the presence of ingredients commonly used in cosmetic formulations. This can be a serious issue when applied as a thin layer to a relatively large surface area of the skin and also with regard to shelf life potency of retinol containing products.

Retinol can also be very difficult to release and drive effectively into the skin from prior art delivery systems, resulting in greatly reduced efficiency of delivery even with relatively high concentrations of retinol in the formulation. Accordingly, although a first formulation may include a higher concentration of a retinoid or retinol than a second formulation, the latter may be more efficient with respect to delivery of the retinoid or retinol if its formulation provides enhanced release and transdermal penetration of the active agent, retinoid or retinol as compared to the former.

Retinol can also be irritating to the skin, discouraging continued application by those in need of treatment with retinol-containing formulations, and thereby reducing if not eliminating efficacy of the treatment. Available retinoid and retinol formulations include solvent-based systems, ointments, water-based formulations, emulsions, gels and lotions, all of which vary in their stability and their efficiency. As such, retinoid and retinol formulations are underutilized for skin care procedures, due to the propensity to cause irritation.

Accordingly, there is a need in the art for topical formulations and delivery systems that can provide retinoids and/or other active agents to the skin of those in need thereof that may alleviate and ameliorate one or more of the exemplary conditions noted above or others that are recognized in the field of dermatological and cosmetic skincare procedures.

The present disclosure provides formulations and delivery systems for retinol, and other members of the retinoid family, and for other skincare active agents, such as known in the art of skincare formulations. Certain embodiments maintain product stability, exhibit low irritancy, and/or provide increased efficiency of release and delivery of the active agents, such as retinol or another member of the retinoid family and/or other active agents.

SUMMARY

In certain embodiments, the present disclosure provides skincare treatment formulations having active agents and transdermal delivery and cutaneous activation and solvent systems, and more particularly, retinol formulations. The skincare formulations exhibit product stability, low irritancy and improved efficiency of delivery of the formulated active agents. In particular, the present disclosure provides a delivery system that exhibits product stability, low irritancy and improved efficiency of delivery of the formulated retinol.

The inventors believe, without wishing to be bound by theory, that certain skincare formulations disclosed herein provide surprising, unexpected results, as noted in a clinical study against a prescription skin treatment active agent, due to a solvent combination of certain embodiments of the present disclosure. The results of the clinical study were stronger than expected. In this study, low-dose, consumer, take-home, cosmetic retinol formulations were used, and novel solvent combinations, including a new solvent that works counter-intuitively. Since retinol is not that soluble in this new solvent, the inventors discovered special phasing preparation process to get it to work. As a result, the inventors were able to get certain retinol formulations to perform better than the prescription drug tretinoin. The clinical study, discussed in further detail below, used Ortho's Retin-A brand and the inventors had comparable or better efficacy while scoring better than the prescription active agent regarding irritation and consumer preference in the tested embodiment.

The present disclosure in certain embodiments provides topical formulations having one or more skin treatment active agent (such as a retinoid such as retinol) and an activation solvent system. The solvent system may comprise one or more of isopentyldiol, dimethyl isosorbide, or a non-ionic surfactant. The formulation may also include one or more of an antioxidant, a xanthine, a moisturizer, and an emollient. In one embodiment, the formulation further comprises an antioxidant.

The skin treatment active agents may be one or more of retinoids, steroids, skin lightening agents, hydroquinone, acne medications, salicylic acid, kojic acid, resorcinol, hexylresorcinol, benzoyl peroxide, sulfur, anti-aging agents, peptides, growth factors, alpha hydroxy acids, enzymes, DNA repair enzymes, vitamins, anti-itch agents, cooling agents, menthol, analgesics, essential oils, anti-inflammatories, anti-pruritics, hydrating agents, osmotic agents, natural moisturizing factor, urea, emollients, occlusives, amino acids, exfoliants, skin conditioning agents, cleansing agents, sebum reducing agents, anti-infectives, hair restoration agents, active agents prone to oxidation, polar and non-polar skin treatment agents, herbal active agents, bakuchiol, therapeutic natural oils, essential oils. In one embodiment, the skin treatment active agent comprises retinol and/or derivatives thereof. In one embodiment, the skin treatment active agent comprises retinol.

The non-ionic surfactant may be one or more of ethoxylates, fatty ethoxylates, propoxylate, block copolymers, poloxamers, polyglyceryl esters, polyglyceryl emulsifiers, sorbitol anhydrides, dipolar agents, phenolic non-ionics.

The non-ionic surfactant may be polysorbate 80 and the antioxidant may be one or more of green tea polyphenols, extracts of licorice, resveratrol, silymarin, curcuminoids, caffeine, astaxanthin, flavones, flavonoids, flavanols, tocopherols, ascorbates, coenzyme Q10, ergothioneine, glutathione, ectoin, bisabolol, emblica.

In certain embodiments, the formulation further includes polysorbate 20.

In certain embodiments, the instant disclosure is directed to methods for therapeutic treatment of a dermatological condition, which methods include topically applying to an affected area a therapeutically effective amount of a topical formulation having a skin treatment active agent as disclosed herein. In certain embodiments, the formulation comprises an activation solvent system comprising isopentyldiol, dimethyl isosorbide, and a non-ionic surfactant.

The affected area may be one or more of human skin, scalp, hair or nails. In one aspect of this disclosure the skin is human skin. In other aspects of the present disclosure, the skin is that of a companion animal, a domestic animal, or a commercially useful animal.

The disclosed activation solvent systems may also comprise one or more solubilizing agents, rheology modifiers, emulsifiers and/or dispersion aids. In one aspect of this embodiment, the solubilizing agent/emulsifier is a non-ionic solubilizing agent/emulsifier.

The disclosed formulations may also comprise at least one retinoid source. In one aspect of this embodiment, the retinoid may be retinol, retinaldehyde, an ester of retinol, including, e.g., palmitate and stearate esters of retinol, retinoic acid, tretinoin or a synthetic retinoid such as adapalene, bexarotene, tazarotene or a combination of two or more thereof. In one aspect of this embodiment, the retinoid is retinol. In another aspect, the retinoid is all trans-retinol.

The disclosed formulations may also comprise one or more antioxidants. In one aspect of this embodiment, the antioxidant is a polyphenol. In a more specific aspect of this embodiment, the antioxidant comprises a polyphenol isolate of *Camellia sinensis*. In a further aspect, the antioxidant comprises 90% or 95% polyphenol isolate of *Camellia sinensis*.

The disclosed formulations may also comprise a xanthine related compound, polymeric derivative thereof, or mixture of xanthine-related materials that can function as antioxidants or stimulators of antioxidant activity. In one specific aspect, the xanthine-related compound is caffeine.

In certain embodiments, the disclosed formulations may also include bakuchiol.

The disclosed formulations may also comprise one or more emollients. In one aspect of this embodiment the emollient is an ester or oil. In various aspects of this embodiment, the emollient can include one or more of the following shea butter, cocoa butter, mineral oil, lanolin, petrolatum, paraffin, beeswax, squalene, cetyl alcohol, olive oil, triethylhexanoin, coconut oil, jojoba oil, sesame oil, almond oil, or other plant oils, and combinations of two or more thereof.

In certain embodiments, the instant disclosure may be directed to methods for preparing the topical formulations described herein. The method may include forming a first mixture of an antioxidant system and an activation solvent system comprising isopentyldiol, dimethyl isosorbide, and a non-ionic surfactant; separately combining an active agent, e.g., retinol, with isopentyl diol and dimethyl isosorbide to form an active agent mixture; and combining the first mixture with the active agent mixture. In certain embodiments, the method is performed under inert atmosphere.

BRIEF DESCRIPTION OF DRAWINGS

The drawings, described below, are for illustrative purposes only and are not necessarily drawn to scale. The drawings are not intended to limit the scope of the disclosure in any way. Wherever possible, the same or like reference numbers will be used throughout the drawings to refer to the same or like parts.

DETAILED DESCRIPTION

Figure 1:
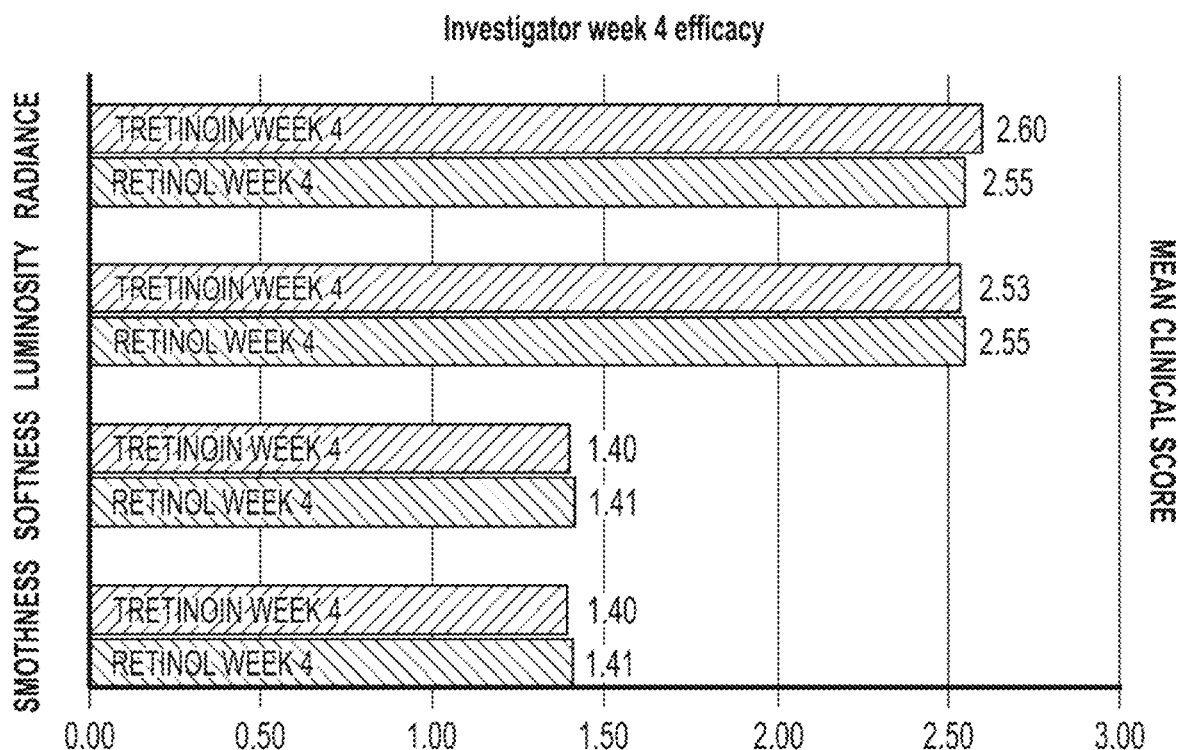
FIG. 1 illustrates an investigator week 4 efficacy chart in terms of mean clinical scores for smoothness, softness, luminosity, and radiance, of skin treated with a formulation according to certain embodiments described herein as compared to a comparative tretinoin formulation.

The present disclosure provides skincare formulations, delivery systems and methods of use thereof for treating, alleviation or amelioration of dermatological conditions amenable to treatment with retinoids, including retinol, and other skin treatment active agents. Amenable conditions include, without limitation, inflammatory disorders of the skin and skin conditions characterized by increased cell turnover including psoriasis, photoaging, weather-beaten appearance, yellowing, loss of elasticity, loss of collagen rich appearance and/or youthfulness, redness, dryness, age spots, skin wrinkles, acne, rosacea, ichthyosis, as well as skin cancers. The disclosed formulations are also useful for improvement in one or more aesthetic criteria, including, but not limited to, a perceived improvement in apparent skin age, skin tone, weather-beaten appearance, yellowing, loss of elasticity, redness, dryness, age spots, skin wrinkles, skin smoothness, brightness, radiance, as well as skin pores becoming less noticeable.

As used herein, the terms "treatment" or "treating" with respect to a skin condition generally means administration with the intent to provide a pharmacodynamics effect, regardless of the outcome. In certain embodiments, "treatment" or "treating" means "having positive effect on a skin condition" and encompass reduction, amelioration, and/or alleviation of at least one symptom of a skin condition, a reduction, amelioration, and/or alleviation in the severity of the skin conditions, delay, prevention, or inhibition of the progression of the skin condition, or a perceived improvement or benefit as a result of the treatment. It may also mean achieving treatment results comparable or better to that of a prescription drug with a non-prescription product. Treatment, as used herein, therefore does not require total curing of the condition. In certain embodiments, a formulation or delivery system of the present disclosure may reduce the severity of a skin condition, reduce the severity of symptoms associated therewith, provide improvement to a patient's quality of life, or delay, prevent, inhibit the onset of one or more symptoms of a skin condition, or provide a perceived benefit. As used herein, these terms also encompass aesthetic improvements to the skin upon application of the disclosed active agents containing formulations.

As used herein, the terms "application," "apply," and "applying" with respect to a disclosed topical formulation, or method of using a disclosed topical formulation, refer to any manner of administering a topical formulation to the skin of a patient which, in medical or cosmetology practice, delivers the formulation to the patient's skin surface. Smearing, rubbing, spreading, spraying a disclosed topical formulation, with or without the aid of suitable devices, on a patient's skin are all included within the scope of the term "application," as used herein. The terms "topical" or "topically" with respect to administration or application of a disclosed formulation refer to epicutaneous administration or application, or administration onto skin.

As used herein, the phrase "effective amount" refers to an amount of a formulation, or component thereof, effective to alleviate or ameliorate a skin condition as noted above, including a range of effects, from a detectable local improvement in an area of topical application to substantial relief of symptoms to an improvement in one or more aesthetic criteria, including, but not limited to, a perceived improvement in damage from free radicals from sunlight (UVB, UVA, Visible Light), HEV (blue) light, Infrared (IR), pollution, irritants, allergens, or various environmental toxins, apparent skin age, radiation damage, sun or UV damage, skin tone, weather-beaten appearance, yellowing, appearance of fine lines, skin roughness, skin sagging, skin firmness, dryness, age spots, skin wrinkles, skin smoothness, brightness, radiance, as well as skin pores becoming less noticeable, hyperpigmentation, scars, skin surface irregularities, rosacea, acne, psoriasis, skin's regenerative and renewal process, redness, ichthyosis, severity of photodamage, lack of tactile smoothness, lack of visual smoothness, lack of softness, lack of luminosity, lack of radiance, skin texture, fine facial wrinkles, crow's feet, dyschromia, crepey skin texture, reduction in skin elasticity, and other damaging skin conditions. The effective amount will vary with the particular condition or conditions being treated, the severity of the condition, the duration of the treatment, the specific components of the composition being used, and other factors. In certain embodiments, the disclosed compositions and formulations provide a method for stabilizing and delivering active agents (e.g., retinoids, including retinol) in an efficacious manner to the skin. Certain disclosed retinoid compositions, formulations, delivery system, and methods of use thereof may reduce, minimize, or eliminate normally-observed retinoid-induced dermatoses including, inter alia, itching, severe skin flaking, breakdown of the skin barrier, discomfort, extreme dryness, cracking of the skin and sensitization. In certain embodiments, the disclosed compositions, formulations, delivery system, and methods of use thereof also provide aesthetic improvements in the skin, including but not limited to skin that appears younger, skin exhibiting a more even tone, skin in which the pores are less noticeable, and skin that is judged by the user to be smoother, and/or to be improved with respect to its weather-beaten or aged appearance, yellowing, loss of elasticity, redness, dryness, age spots, and/or skin wrinkles.

In certain embodiments, the activation and solvent systems disclosed herein not only maintain product stability, including stability of the formulated active agent (e.g., retinoid) as well as the antioxidant, but it also provide a greater efficiency of the active agent. In this, in certain embodiments, the inventors surprisingly have found effectiveness of certain disclosed formulations in comparison with typical home use skincare formulations and comparable with prescription active agents. As such, the certain disclosed retinoid formulations, and methods of use thereof, function effectively in skincare treatments in their own right at a non-prescription strength, as compared with prescription strength active agents, as discussed in more detail hereinafter. In certain embodiments, the formulations cause reduced, minimal or no skin irritation and other possible side effects typically associated with such formulations, especially in daily, long term use.

The antioxidant can be a polyphenol that is isolated from plants, chemically synthesized; the antioxidant can also be a semi-synthetic compound prepared by modification of a natural polyphenol or mixture of polyphenols. In certain embodiments of the present disclosure, the antioxidant includes "green tea polyphenols" isolated and purified from the leaves of *Camellia sinensis* plants. These antioxidants, as formulated and delivered herein, may provide antioxidant activity or anti-inflammatory activity, and, further, may provide skin soothing, protection, anti-irritant, or repair activity. Inventors unexpectedly have found that in certain embodiments, the presence of antioxidants, e.g., polyphenols, in the manner disclosed herein in retinoid formulations of the present disclosure provide better toleration with respect to the retinoid formulations, i.e., reduces and/or eliminates irritation or redness arising from use of the formulations as, e.g., daily use non-prescription products.

In certain embodiments, the present disclosure provides formulations comprising one or more retinoids, including retinol, that are useful in the disclosed delivery system. Certain disclosed formulations may provide retinoid stability, low irritancy, or efficient release of the active agent retinoid/retinol, when applied to the skin. In one aspect of this disclosure, the skin is human skin. In other aspects of the present disclosure, the skin is that of a companion animal, a domestic animal, or a commercially useful animal.

Inventors further believe, without wishing to be bound by theory, that unexpected results associated with certain embodiments of the retinoid/retinol formulations are obtained by the synergistic operation of the activation and solvent systems herein, i.e., the functioning of the activation and solvent systems resulting in control release of the retinoid active agent(s). In this, the disclosed formulations of certain embodiments release the active agents at maximum, optimum strength and rate of release with minimal or no irritation to the skin.

The disclosed formulations may also comprise at least one retinoid source. In one aspect of this embodiment, the retinoid may be retinol, retinoic acid, tretinoin, retinaldehyde, an ester of retinol or of retinoic acid, including, e.g., palmitate, acetate, propionate, butyrate, hexanoate, heptanoate, caprylate, and stearate esters of retinol or retinoic acid, or a synthetic retinoid such as, but not limited to, adapalene, bexarotene, tazarotene, or a combination of two or more thereof. The retinoid or retinol is an oily substance that is solubilized by the formulations disclosed herein. In one aspect of this embodiment, the retinoid is retinol. In another aspect the retinoid is all trans-retinol (i.e., tretinoin). In one embodiment, retinol and/or derivatives thereof is/are the sole active agent in the formulation. In another embodiment, retinol and/or derivatives thereof in combination with another active agent (e.g., bakuchiol) are the sole active agents in the formulations described herein, although the present invention is not limited to the number of active agents.

In particular embodiments, formulations and delivery systems of the present disclosure comprise about 0.01 wt % to about 1.0 wt % retinol and/or one or more derivatives thereof, based on total weight of the formulation. In various aspects of these embodiments, formulations and delivery systems of the present disclosure comprise about 0.02 wt % to about 1.0 wt %, about 0.03 wt % to about 1.0 wt %, about 0.04 wt % to about 1.0 wt %, about 0.05 wt % to about 1.0 wt %, about 0.06 wt % to about 1.0 wt %, about 0.07 wt % to about 1.0 wt %, about 0.08 wt % to about 1.0 wt %, about 0.09 wt % to about 1.0 wt %, about 0.1 wt % to about 1.0 wt %, about 0.2 wt % to about 1.0 wt %, about 0.3 wt % to about 1.0 wt %, about 0.4 wt % to about 1.0 wt %, or about 0.5 wt % to about 1.0 wt % retinol and/or one or more derivatives thereof, based on total weight of the formulation. Such formulations and delivery systems can be, for example, those used in consumer products.

In specific aspects of these embodiments, formulations and delivery systems of the present disclosure comprise about 0.1 wt %, about 0.2 wt %, 0.3 wt %, 0.5 wt %, 0.75 wt %, or 1.0 wt % retinol and/or one or more derivatives thereof, based on the total weight of the formulation.

In particular embodiments, formulations and delivery systems of the present disclosure, comprise about 1.0 wt % to 50 wt % retinol and/or one or more derivatives thereof. Such formulations and delivery systems can be, for example, those used by physicians in in-office procedures.

Retinoids are some of the most effective anti-aging ingredients used in over-the-counter (OTC) cosmeceutical moisturizers. These OTC retinoids include retinyl esters, retinol, and retinaldehye, which are interconvertible. Retinyl esters can be hydrolyzed to retinol which may be oxidized to retinaldehyde and then oxidized again to retinoic acid, also known as tretinoin, within keratinocytes. The anti-aging activity of the retinoids can be summarized as:

retinoic acid>retinaldehyde>retinol>>>retinyl esters

Unfortunately, the tolerability ranking is the exact opposite:

retinyl esters>retinol~retinaldehyde>>retinoic acid

The accompanying irritation, especially noted with retinoic acid and retinaldehyde, is believed to be due to an overload of the retinoic acid-dependent pathways with supra-physiological amounts of exogenous retinoic acid in the skin. Thus, the poor tolerability of the retinoids has limited their use.

In certain embodiments, derivatives of retinol may include one or more of retinaldehyde, retinyl esters, or tretinoin (retinoic acid). In certain embodiments, formulations and delivery systems described herein may include less than about 50 wt %, less than about 40 wt %, less than about 30 wt %, less than about 20 wt %, less than about 15 wt %, less than about 10 wt %, less than about 8 wt %, less than about 5 wt %, less than about 3 wt %, less than about 1 wt %, or substantially no (e.g., 0 wt %), tretinoin (retinoic acid), based on total weight of the retinol and derivatives thereof in the formulation and delivery systems described herein.

Inventors believe, without wishing to be bound by theory, that in certain embodiments, the increased efficiency of delivery of the active agent retinoid (e.g., retinol and/or derivatives thereof) coupled with the marked reduction in irritation observed upon administration of the presently disclosed retinoid formulations, permit the formulation and use of retinoid systems with significantly higher concentrations of retinoid (e.g., retinol and/or derivatives thereof) than previously employed. As such, certain disclosed retinoid formulations and delivery systems provide effective skincare treatments at non-prescription strength, all while also being gently and well-tolerated by consumers.

Inventors believe, without wishing to be bound by theory, that in certain embodiments, the retinoid, retinol, and/or all trans-retinol of the presently disclosed formulations and delivery systems contributes to one or more of an increase in skin cell turnover, support of collagen production in the skin, and brightening of areas of hyperpigmentation of the skin. As such, inventors further believe, without being bound by theory, that such beneficial skin activity in certain embodiments may be a consequence of different genes that are switched on by the retinoid/retinol formulations disclosed herein.

Inventors similarly believe that, in certain embodiments as formulated and delivered herein, the pure and active form of vitamin A, i.e., all trans-retinol, provide one or more of effective topical treatment, a low incidence of irritation, support of the skin barrier, or an increased cell turnover in the skin. This may cause one or more of a reduction in the appearance of fine lines, wrinkles, or age spots, as well as improving skin texture or tone or promoting a collagen-rich appearance. As used herein, "pure" refers to potency or activity measured as the percentage content of the referenced component or agent. In certain embodiments, the retinol included in the retinoid/retinol formulations or delivery systems described herein includes at least about 80 wt %, at least about 85 wt %, at least about 90 wt %, at least about 95 wt %, at least about 96 wt %, at least about 97 wt %, at least about 98 wt %, at least about 99 wt %, or at least about 99.5 wt % retinol, based on total weight of the retinol and derivatives thereof in the formulations and delivery systems described herein.

In certain embodiments, retinol can degrade into biologically inactive forms when exposed to light and air, which could reduce its efficacy. It is believed, without being construed as limiting, that the efficacy of retinol in the treatment of the skin conditions described herein depends on its oxidative stability and/or the delivery system that it is formulated in.

In certain embodiments, the formulations and/or delivery systems disclosed herein form an anhydrous micro-emulsion where the retinol and/or derivatives thereof are broken up into the dispersed phase and the solvent system is in the continuous phase. In certain embodiments, the micro-emulsion nature of the formulation is believed to contribute to the stability of the retinol. The term "anhydrous micro-emulsion," as used herein, refers to a micro-emulsion that includes less than about 5 wt % water, less than about 4 wt % water, less than about 3 wt % water, less than about 2 wt % water, less than about 1 wt % water, less than about 0.5 wt % water, or no water (e.g., 0 wt %), based on total weight of the formulation.

In certain embodiments, the solvent system includes a polyol, which may be part of the continuous phase of the micro-emulsion. In certain embodiments, the solvent system includes a diol, which may be part of the continuous phase of the micro-emulsion. Exemplary diols may include, without limitations, one or more of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, isopentyldiol, ethoxydiglycol, or a combination thereof. In one embodiment, the solvent system includes isopentyldiol, which may be part of the continuous phase of the micro-emulsion. In one embodiment, the solvent systems described herein include ethoxydiglycol. In one embodiment, the solvent systems disclosed herein include isopentyldiol and ethoxydiglycol. In certain embodiments, the polyol (e.g., diol such as isopentyldiol) also acts as a humectant by holding water in the skin and creating a smooth film over the skin surface.

In certain embodiments, the diol may be included in the formulations or delivery systems described herein in an amount ranging from any of about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, or about 90 wt %, or any sub-range or single value therein, based on the total weight of the formulation. In certain embodiments, the diol may be included in the formulations or delivery systems described herein in an amount ranging from about 10 wt % to about 90 wt %, from about 25 wt % to about 75 wt %, from about 45 wt % to about 65 wt %, or from about 50 wt % to about 60 wt %, or any sub-range or single value therein, based on the total weight of the formulation.

In certain embodiments, the formulations or delivery systems described herein may include isopentyldiol in an amount ranging from any of about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, or about 90 wt %, or any sub-range or single value therein, based on the total weight of the formulation. In certain embodiments, the formulations or delivery systems described herein may include isopentyldiol in an amount ranging from about 10 wt % to about 90 wt %, from about 25 wt % to about 75 wt %, from about 45 wt % to about 65 wt %, or from about 50 wt % to about 60 wt %, or any sub-range or single value therein, based on the total weight of the formulation.

In certain embodiments, the formulations or delivery systems described herein may include ethoxydiglycol in an amount ranging from any of about 1 wt %, about 5 wt %, about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, or about 80 wt %, or any sub-range or single value therein, based on the total weight of the formulation. In certain embodiments, the formulations or delivery systems described herein may include ethoxydiglycol in an amount ranging from about 1 wt % to about 80 wt %, from about 1 wt % to about 10 wt %, from about 1 wt % to about 5 wt %, or from about 2 wt % to about 3 wt %, or any sub-range or single value therein, based on the total weight of the formulation.

In certain embodiments, the formulations or delivery systems described herein include isopentyldiol and ethoxydiglycol at a weight to weight ratio of from any of about 100:1, about 90:1, about 80:1, about 70:1, about 60:1, about 50:1, about 40:1, about 30:1, about 20:1, about 10:1, or about 5:1 to any of about 1:5, about 1:10, about 1:20, about 1:30, about 1:40, about 1:50, about 1:60, about 1:70, about 1:80, about 1:90, or about 1:100, or any sub-range or single ratio value therein. In certain embodiments, the formulations or delivery systems described herein include isopentyldiol and ethoxydiglycol at a weight to weight ratio of from about 50:1 to about 1:1, about 40:1 to about 10:1, or about 30:1 to about 20:1, or any sub-range or single ratio value therein.

In certain embodiment, the solvent system in the formulations or delivery systems described herein further includes a dimethyl isosorbide. In certain embodiments, the formulations or delivery systems described herein may include dimethyl isosorbide (DMI) in an amount ranging from any of about 5 wt %, about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, or about 90 wt %, or any sub-range or single value therein, based on the total weight of the formulation. In certain embodiments, the formulations or delivery systems described herein include DMI in an amount from about 5 wt % to about 90 wt %, from about 15 wt % to about 60 wt %, from about 20 wt % to about 40 wt %, or from about 25 wt % to about 35 wt %, or any sub-range or single value therein, based on the total weight of the formulation.

In certain embodiments, the formulations or delivery systems described herein include a diol and DMI at a weight to weight ratio of from any of about 20:1, about 15:1, about 10:1, about 8:1, about 5:1, about 3:1, or about 2:1 to any of about 1:2, about 1:3, about 1:5, about 1:8, about 1:10, about 1:15, or about 1:20, or any sub-range or single ratio value therein. In certain embodiments, the formulations or delivery systems described herein include a diol and DMI at a weight to weight ratio of from about 20:1 to about 1:1, about 10:1 to about 1:1, or about 3:1 to about 1:1, or any sub-range or single ratio value therein.

In certain embodiment, the solvent system of the formulations or delivery systems described herein further includes a surfactant, such as a non-ionic surfactant. Exemplary suitable non-ionic surfactants include, without limitations, one or more of ethoxylates, fatty ethoxylates, propoxylate, block copolymers, poloxamers, polyglyceryl esters, polyglyceryl emulsifiers, sorbitol anhydrides, dipolar agents, phenolic non-ionics, or a combination thereof. In certain embodiments, the non-ionic surfactant in the formulations described herein includes polysorbate 80.

In certain embodiments, the formulations or delivery systems described herein may include a surfactant (e.g., non-ionic surfactant) in an amount ranging from any of about 1 wt %, about 3 wt %, about 5 wt %, about 8 wt %, about 10 wt %, about 15 wt %, or about 20 wt % to any of about 25 wt %, about 30 wt %, about 35 wt %, or about 40 wt %, or any sub-range or single value therein, based on the total weight of the formulation. In certain embodiments, the formulations or delivery systems described herein include a surfactant (e.g., non-ionic surfactant) in an amount ranging from about 1 wt % to about 40 wt %, from about 3 wt % to about 15 wt %, from about 6 wt % to about 10 wt %, or from about 7 wt % to about 9 wt %, or any sub-range or single value therein, based on the total weight of the formulation.

In certain embodiments, the formulations or delivery systems described herein may include a polysorbate 80 in an amount ranging from any of about 1 wt %, about 3 wt %, about 5 wt %, about 8 wt %, about 10 wt %, about 15 wt %, or about 20 wt % to any of about 25 wt %, about 30 wt %, about 35 wt %, or about 40 wt %, or any sub-range or single value therein, based on the total weight of the formulation. In certain embodiments, the formulations or delivery systems described herein include a polysorbate 80 in an amount ranging from about 1 wt % to about 40 wt %, from about 3 wt % to about 15 wt %, from about 6 wt % to about 10 wt %, or from about 7 wt % to about 9 wt %, or any sub-range or single value therein, based on the total weight of the formulation.

In certain embodiments, the formulations or delivery systems described herein include a diol (e.g., isopentyldiol and/or ethoxydiglycol) and a surfactant (e.g., polysorbate 80) at a weight to weight ratio of from any of about 20:1, about 15:1, or about 10:1 to any of about 8:1, about 5:1, about 3:1, or about 1:1, or any sub-range or single ratio value therein. In certain embodiments, the formulations or delivery systems described herein include a diol and a surfactant at a weight to weight ratio of from about 20:1 to about 1:1, about 10:1 to about 1:1, or about 5:1 to about 1:1, or any sub-range or single ratio value therein.

The disclosed formulations also comprise one or more solubilizing agents and/or emulsifiers and/or dispersants. In one aspect of this embodiment, the solubilizing agent/emulsifier/dispersant is a non-ionic solubilizing agent/emulsifier/dispersant.

In certain embodiments, the formulations described herein further include bakuchiol. It is believed, without being construed as limiting, that the bakuchiol potentiates the retinol in certain embodiments. Bakuchiol, derived from the Psoralea corylifolia seed, is a relatively new ingredient to dermatology possessing antioxidant, anti-inflammatory, and antibacterial properties. It is not a retinoid and remains photostable in certain embodiments. It is believed to possess retinol-like functionality through retinol-like regulation of gene expression inducing upregulation of collagen types I, III, and IV and extracellular matrix synthesis enzymes.

One of the challenges associated with retinol formulations is getting the retinol to preform and penetrate through the skin without causing irritation. In certain embodiments, the solvent systems described herein contribute to the enhanced penetration of the retinol into the skin, which is further augmented by bakuchiol, thereby achieving the benefits of tretinoin without the accompanying irritation. In certain aspects, it is believed that bakuchiol may act as a co-solvent for retinol due to the similarity in their chemical structure.

In certain embodiments, formulations described herein may include a retinoid (e.g., retinol) and bakuchiol, e.g., with any of the delivery systems described herein and/or with any of the excipients described.

In certain embodiments, formulations described herein may include bakuchiol at an amount ranging from any of above 0 wt %, about 0.1 wt %, about 0.3 wt %, about 0.5 wt %, about 0.7 wt %, or about 1 wt % to any of about 3 wt %, about 5 wt %, about 7 wt %, about 10 wt %, about 15 wt %, or about 20 wt %, or any sub-range or single value therein, based on total weight of the formulation. In certain embodiments, formulations described herein may include bakuchiol at an amount ranging from above 0 wt % to about 20 wt %, from about 0.1 wt % to about 3 wt %, from about 0.5 wt % to about 2 wt %, or any sub-range or single value therein, based on total weight of the formulation.

In certain embodiments, the weight to weight ratio of the retinol to the bakuchiol ranges from about 10:1 to about 1:10, from about 8:1 to about 1:8, from about 5:1 to about 1:5, from about 3:1 to about 1:3, or from about 2:1 to about 1:2, or any sub-range or single ratio value therein.

In certain embodiments, formulations described herein further include Polysorbate 20 which may complex with and/or solubilize the retinol. In certain embodiments, formulations described herein may include polysorbate 20 at an amount ranging from any of above 0 wt %, about 0.01 wt %, about 0.1 wt %, about 0.3 wt %, about 0.5 wt %, about 0.7 wt %, or about 1 wt % to any of about 3 wt %, about 5 wt %, about 7 wt %, about 10 wt %, about 15 wt %, about 20 wt %, or about 30 wt %, or any sub-range or single value therein, based on total weight of the formulation. In certain embodiments, formulations described herein may include bakuchiol at an amount ranging from above 0.01 wt % to about 30 wt %, from about 0.1 wt % to about 3 wt %, from about 0.2 wt % to about 0.5 wt %, or any sub-range or single value therein, based on total weight of the formulation.

In certain embodiments, the weight to weight ratio of the retinol to the polysorbate 20 ranges from about 10:1 to about 1:10, from about 8:1 to about 1:8, from about 5:1 to about 1:5, from about 3:1 to about 1:3, from about 2:1 to about 1:2, or about 1:1, or any sub-range or single ratio value therein.

In certain embodiments, the formulations described herein provide efficacious delivery of the retinol due to one or more of the constituents of the unique solvent system, such as, the polyol (e.g., diol such as isopentyldiol and/or ethoxydiglycol), DMI, surfactant (such as polysorbate 80), bakuchiol, or a combination thereof. In one embodiment, the efficacy of the solvent system is enhanced through the inclusion of one or more of isopentyldiol, DMI, polysorbate 80, bakuchiol, or a combination thereof.

In certain embodiments, the formulations described herein further include an antioxidant system such as botanical anti-inflammatories to decrease irritation. In certain embodiments, the formulations described herein include, without limitations, one or more of *Camellia Sinensis* polyphenols (green tea), black tea extract, *Glycyrrhiza Glabra* (licorice) root extract, or a combination thereof.

Antioxidants, particularly the green-tea polyphenols, as well as retinol, are generally recognized as notoriously difficult to stabilize, as both are subject to oxidation and/or degradation by oxygen, moisture, light, trace metals, as well as other ingredients frequently included in formulations. This is particularly apparent with respect to topical formulations that present a large surface area when spread on the skin, thereby facilitating air-oxidation of susceptible components of the applied formulation and/or when seeking a stable long-term shelf life of the formulations, for example, 2 years. Surprisingly and unexpectedly, certain disclosed formulations overcome these issues, and provide stable, non or minimal irritating, or efficacious systems for topical application to the skin.

The antioxidant included in the disclosed retinoid formulations may include *Camellia sinensis* (green tea) polyphenols. In particular embodiments, a purified isolate of *Camellia sinensis* (green tea) polyphenols is included in the formulations. The present disclosure contemplates that the purity of the polyphenols may range from trace amounts obtained, for example, from green tea extracts to 100% pure polyphenols. Although, in various embodiments, any *Camellia sinensis* (green tea) preparation of polyphenols may be formulated, in specific aspects of this embodiment, a 90% or 95% purified preparation of *Camellia sinensis* (green tea) polyphenols is formulated. In various other formulations, the amount of polyphenol antioxidant added is inversely related to the purity thereof.

The antioxidant included in the disclosed retinoid formulations may include *Camellia sinensis* (green tea) polyphenols which may be a mixture of polyphenol species. Suitable green tea polyphenols include, but are not limited to, catechins, such as epigallocatechin gallate (EGCG), epigallocatechin (EGC), epicatechin gallate (ECG), and epicatechin (EC), cis and trans isomers thereof, salts thereof, equivalent derivatives thereof, and combinations thereof. In specific aspects, the major component of the formulated polyphenol antioxidant is epigallocatechin gallate (EGCG).

In certain embodiments, the formulations described herein includes an antioxidant system which includes any of the green tea polyphenols described herein in combination with at least one additional antioxidants, such as, without limitations, black tea extract and/or licorice root extract.

In one embodiment, the additional antioxidants in the antioxidant system may be selected from the group of cinnamic acid, ferulic acid, caffeic acid, p-coumaric acid, sinapinic acid, cis and trans isomers thereof, salts thereof, equivalent derivatives thereof, and combinations thereof. In another embodiment, the additional antioxidants in the antioxidant system (and in the topical composition generally) may be free or substantially free of cinnamic acid, ferulic acid, caffeic acid, p-coumaric acid, sinapinic acid, cis and trans isomers thereof, salts thereof, equivalent derivatives thereof, and combinations thereof.

In certain embodiments, the additional antioxidants in the antioxidant system may be selected from the group of gallic acid, delphinidin, luteolin, quercetin, cyanidin, taxifolin, kaempferol, malvidin, hesperidin, pelargonidin, apigenin, naringenin, chrysin, ergothioneine, glutathione, emblica, cis and trans isomers thereof, salts thereof, equivalent derivatives thereof, and combinations thereof.

In certain embodiments, the additional antioxidants in the antioxidant system may be selected from the group of apigenin, ergothioneine, glutathione, emblica, cis and trans isomers thereof, salts thereof, equivalent derivatives thereof, and combinations thereof.

The disclosed formulations may also comprise a xanthine related compound, polymeric derivative thereof, or mixture of xanthine-related materials that can function as antioxidants or stimulators of antioxidant activity. In one specific aspect, the xanthine-related compound is caffeine. In another specific aspect, caffeine of the disclosed formulations and delivery systems is pure, very pure, or USP grade caffeine.

The disclosed formulations may also comprise one or more moisturizers and/or humectants. The disclosed formulations may also comprise one or more emollients. In one aspect of this embodiment, the emollient may be an ester, oil, or silicone. In various aspects of this embodiment, the emollient can include one or more of the following shea butter, cocoa butter, mineral oil, lanolin, petrolatum, paraffin, beeswax, squalene, cetyl alcohol, olive oil, triethylhexanoin, coconut oil, jojoba oil, sesame oil, almond oil, or other plant oils, omega-6 fatty acids, ceramides, primrose oil, grape seed oil, ceramide, and combinations of two or more thereof.

Each of the antioxidants in the antioxidant system may be present, individually or cumulatively, in a concentration of from any of above 0 wt. %, about 0.001 wt %, about 0.01 wt. %, about 0.05 wt. %, about 0.1 wt. %, about 0.15 wt. %, about 0.2 wt. %, about 0.25 wt. %, about 0.3 wt. %, about 0.35 wt. %, or about 0.4 wt. % to any of about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.5 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt %, or about 20 wt %, or any sub-range or single value therein, based on total weight of the formulation.

In certain embodiments, the antioxidant system includes black tea extract that is present in the formulation in an amount ranging from above 0 wt. % to about 20 wt. %, from about 0.001 wt. % to about 5 wt. %, or from about 0.001 wt. % to about 0.5 wt. %, or any sub-range or single value therein, based on total weight of the formulation.

In certain embodiments, the antioxidant system includes licorice root extract that is present in the topical composition in an amount ranging from above 0 wt. % to about 20 wt. %, from about 0.001 wt. % to about 5 wt. %, or from about 0.001 wt. % to about 0.5 wt. %, or any sub-range or single value therein, based on total weight of the formulation.

In certain embodiments, the antioxidant system includes green tea polyphenols in an amount ranging from about 0.1 wt. % to about 15 wt. %, from about 0.1 wt. % to about 5 wt. %, or from about 0.5 wt. % to about 2 wt. %, or any sub-range or single value therein, based on total weight of the formulation.

In certain embodiments, the antioxidant system includes xanthine (e.g., caffeine) in an amount ranging from about 0.01 wt. % to about 10 wt. %, from about 0.1 wt. % to about 5 wt. %, or from about 0.5 wt. % to about 2.5 wt. %, or any sub-range or single value therein, based on total weight of the formulation.

In certain embodiments, the antioxidant system includes, comprises, consists, or consists essentially of a combination of any of the green tea polyphenols described herein and at least one of xanthine (e.g., caffeine), black tea extract, and licorice root extract in an (individual or cumulative) concentration of from any of above 0 wt. %, about 0.001 wt %, about 0.01 wt. %, about 0.05 wt. %, about 0.1 wt. %, about 0.15 wt. %, about 0.2 wt. %, about 0.25 wt. %, about 0.3 wt. %, about 0.35 wt. %, or about 0.4 wt. % to any of about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.5 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt %, or about 20 wt %, or any sub-range or single value therein, based on total weight of the formulation.

In certain embodiments, the weight to weight ratio of the green tea polyphenols to the one or more additional antioxidants (e.g., xanthine (e.g., caffeine), black tea extract, and licorice root extract), cumulatively, ranges from about 10:1 to about 1:10, about 8:1 to about 1:8, about 5:1 to about 1:5, about 3:1 to about 1:3, about 2:1 to about 1:2, or about 1:1.

The present inventors have noted that certain embodiments provide not only potent antioxidant reduction of reactive oxygen species (ROS) but they also provided, very surprisingly, a reduction in the irritation normally associated with retinol use. This observed reduction in the irritation in certain embodiments was dramatically better than other formulations. Inclusion of these materials in certain disclosed formulations may boost patient compliance. As documented in the trials presented below, patients stay on the treatment regimen because they are not or minimally irritated. Thus, although irritation is a major problem with topical retinol applications, it was not observed or minimally observed upon testing with certain presently disclosed retinoid systems.

In further embodiments, the all trans-retinol of the above described formulations can be substituted with or supplemented by one or more of the following retinoids at the indicated percentage by weight (% w/w) levels: retinaldehyde (0.01%-1%), esters of retinol (0.01-5%), retinoic acid (0.01%-0.2%), synthetic retinoids, e.g., adapalene (0.02-0.5%), tazarotene (0.01%-0.2%).

In still further embodiments, the all trans-retinol of the above described formulations can be substituted with or supplemented by one or more of the following retinoids at the indicated (% w/w) levels: retinaldehyde (0.05-0.10%), esters of retinol (0.1-2%), retinoic acid (0.02%-0.15%), synthetic retinoids, e.g., adapalene (0.1-0.3%), tazarotene (0.05%-0.1%).

In certain embodiments, the dosage of the formulation of the present disclosure to be applied to the skin is within the range of from 0.01 g to 5 g, from 0.02 g to 4 g, from 0.05 g to 3 g, from 0.1 g to 2 g, from 0.2 g to 1 g. In one aspect of these embodiments, the dosage of the formulation of the present disclosure to be applied to the skin can be 0.4 g. The actual dosage applied will depend on, inter alia, the condition to be treated, the particular regimen to be followed, and the personal preferences of the user. For example, different dosages may be used for spot treatment, multi-spot treatment, full or partial face treatment, treatment of parts of the body, such as neck, hands, among others.

In certain embodiments, the formulation includes at least one additional cosmetically acceptable excipient. Exemplary cosmetically acceptable excipients, include, without limitations, epidermal penetration enhancer, solvent, mild surfactants, oil bodies, emulsifiers, pearlescent waxes, consistency regulators, thickeners, rheology modifiers, suspending agents, chelating agents, preservatives, super fatting agents, stabilizers, polymers, silicone or siloxane compounds (e.g., caprylyl methicone, PEG/PPG-18/18 dimethicone), fats, waxes, lecithins, phospholipids, UV photoprotective factors, biogenic active ingredients, additional antioxidants, deodorants, antiperspirants, antidandruff agents, film formers, swelling agents, insect repellents, self-tanning agents, tyrosinase inhibitors, hydrotropes, solubilizers, perfume oils, dyes, zinc oxide, fatty alcohols, esters of fatty acids, adjuvants, Natural or Synthetic Triglycerides Including Glyceryl Esters and Derivatives, hydrocarbon oils, super-fatting agents, polymers, biogenic active ingredients, hydrotropic agents, bacteria-inhibiting agents, colorants, UV screening agents, agents that absorb UV light and provide photo protection to the skin, or combinations thereof.

Additional Cosmetically Acceptable Excipients

In certain embodiments, the cosmetically acceptable excipient includes natural gums (e.g., a natural plant gum). Suitable natural gums include, without limitations, guar gum, carob gum, konjac gum, xanthan gum, *sclerotium* gum, acacia gum, cellulose gum (modified or not), or a combination thereof.

In certain embodiments, the cosmetically acceptable excipient includes an emulsifier. Suitable emulsifiers include, without limitations, PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, lsosteareth-20, Ceteareth-20, Oleth-20, Steareth-20, Steareth-21, Ceteth-20, lsoceteth-20, Laureth-23, Steareth-100, Glyceryl Stearate Citrate, Glyceryl Stearate SE (self-emulsifying), stearic acid, salts of stearic acid, polyglyceryl-3-methylglycosedistearate, or a combination thereof.

Further suitable emulsifiers are phosphate esters and the salts thereof such as cetyl phosphate (Amphisol® A), diethanolamine cetyl phosphate (Amphisol®DEA), potassium cetyl phosphate (Amphisol® K), sodium cetearyl sulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobutene. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

In certain embodiments, the cosmetically acceptable excipient includes a chelating agent. Suitable chelating agents include, without limitations, disodium ethylenediaminetetraacetic acid (EDTA), diethylenetriaminepentaacetic acid (DTPA), N-(hydroxyethyl)-ethylenediaminetriacetic acid (HEDTA), and nitrilotriacetic acid (NTA).

In certain embodiments, the cosmetically acceptable excipient includes additional antioxidants such as a form of Vitamin E. Suitable forms of Vitamin E that may be included in the topical composition can be selected from alpha, beta, delta, and gamma tocopherols, and alpha, beta, delta and gamma tocotrienols, and combinations thereof.

In certain embodiments, the cosmetically acceptable excipient in the topical composition includes a preservative. Suitable preservative agents include, for example, phenoxyethanol, a solution of paraben, pentanediol and sorbic acid, as well as silver complexes which are known under the commercial reference Surfacine® and other classes of substances set out in annex 6, parts A and B of the cosmetic regulations, i.e. a suitable preservative.

In certain embodiments, the cosmetically acceptable excipient includes a perfume oil. Suitable perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace,

*angelica*, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (*galbanum*, elemi, benzoin, myrrh, olibanum, opoponax). Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams.

Essential oils of relatively low volatility, which are mostly used as aroma components, are also suitable as perfume oils, e.g. sage oil, chamomile oil, oil of cloves, melissa oil, mint oil, cinnamon leaf oil, linden blossom oil, juniper berry oil, vetiver oil, olibanum oil, *galbanum* oil, labolanum oil and lavandin oil. Other suitable oils include bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

In certain embodiments, the cosmetically acceptable excipient includes a perfume oil that is an essential oil selected from the group of a lavender oil, a bergamot oil, a *eucalyptus* oil, a chamomile oil, a *melaleuca* oil, or a combination thereof. In one embodiment, the cosmetically acceptable excipient includes a lavender oil, a chamomile oil, or a combination thereof.

In certain embodiments, the perfume oil (each perfume oil individually or all perfume oils in the topical composition cumulatively) is present in the topical composition an amount of above 0 wt. % to about 5 wt. %, from above 0 wt. % to about 1 wt. %, or from about 0.01 wt. % to about 0.3 wt. %, based on total weight of the topical composition.

In certain embodiment, the pH of the topical composition ranges from any of about 2.0, about 2.1, about 2.2, about 2.3, about 2.4, about 2.5, about 2.6, about 2.7, about 2.8, about 2.8, or about 2.9 to any of about 3.0, about 3.1, about 3.2, about 3.3, about 3.4, about 3.5, about 3.6, about 3.7, about 3.8, about 3.8, about 3.9, or about 4.0. In certain embodiments, the pH of the topical composition is about 2.0 to about 4.0, about 2.5 to about 3.5, or about 2.7 to about 3.3.

The formulations described herein may be formulated in any dermatological acceptable form such as a serum, emulsion, cream, foam, spray, ointment, gel, lotion, or as a pad or roll-on applied formulation, which may contain ingredients to improve, modify, or stabilize the composition physically or cosmetically.

The formulations according to the disclosure may also contain one or one more additional cosmetically acceptable excipients as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerization of unsaturated fatty alcohols).

Examples of such ester oils are isopropyl myristate, isopropyl palmitate, isopropyl stearate, isopropyl isostearate, isopropyl oleate, n-butyl stearate, n-hexyl laurate, n-decyl oleate, isooctyl stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants

Diethylhexyl 2,6-naphthalate, di-n-butyl adipate, di(2-ethylhexyl)-adipate, di(2-ethyl hexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

Natural or Synthetic Triglycerides Including Glyceryl Esters and Derivatives

Di- or triglycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borage oil, etc.

Waxes including esters of long-chain acids and alcohols as well as compounds having wax-like properties, e.g., carnauba wax, beeswax (white or yellow), lanolin wax, candelilla wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially lauryl and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethylene glycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycol ether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesqui-isostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/0 emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropyene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylamino-propyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkyl betaine, N-alkylaminobetaines. Alkylimidazolines, alkylopeptides, lipoaminoacides, self-emulsifying bases and the compounds as described in K. F. DePolo, A short textbook of cosmetology, Chapter 8, Table 8-7, p 250-251.

Nonionic bases such as PEG-6 beeswax (and) PEG-6 stearate (and) polyglyceryl-2-isostearate, glyceryl stearate (and) PEG-100 stearate, PEG-5 glyceryl stearate, sorbitan oleate (and) polyglyceryl-3 ricinoleate, sorbitan stearate and sucrose cocoate, glyceryl stearate and laureth-23, cetearyl alcohol and ceteth-20, cetearyl alcohol and polysorbate 60 and PEG-150 and stearate-20, cetearyl alcohol and cetearyl polyglucoside, cetearyl alcohol and ceteareth-20, cetearyl alcohol and PEG-40 castor oil, cetearyl alcohol and PEG-40 castor oil and sodium cetearyl sulfate, stearyl alcohol and steareth-7 and steareth-10, cetearyl alcohol and szeareth-7 and steareth-10, glyceryl stearate and PEG-75 stearate, propylene glycol ceteth-3 acetate, propylene glycol isoceth-3 acetate, cetearyl alcohol and ceteth-12 and oleth-12, PEG-6 stearate and PEG-32 stearate, PEG-6 stearate and ceteth-20 and steareth-20, PEG-6 stearate and ceteth-20 and glyceryl stearate and steareth-20, glyceryl stearate and ceteareth-20.

Anionic alkaline bases such as PEG-2 stearate SE, glyceryl stearate SE, propylene glycol stearate. Anionic acid bases such as cetearyl Alcohol and Sodium cetearyl sulfate, cetearyl alcohol and sodium lauryl sulfate, trilaneth-4 phosphate and glycol stearate and PEG-2 stearate, glyceryl stearate and sodium lauryl Sulfate. Cationic acid bases such as cetearyl alcohol and cetrimonium bromide.

Adjuvants and Additives

The cosmetic sunscreen compositions, for example creams, gels, lotions, alcoholic and aqueous/alcoholic solutions, emulsions, wax/fat compositions, stick preparations, powders or ointments, may in addition contain, as further adjuvants and additives such as, mild surfactants, super-fatting agents, consistency regulators, thickeners, polymers, stabilizers, biogenic active ingredients, swelling agents, further UV light-protective factors, antioxidants, hydrotropic agents, preservatives, self-tanning agents, solubilizers, perfume oils, colorants, bacteria-inhibiting agents and the like.

Super-Fatting Agents

Substances suitable for use as super-fatting agents are, for example, lanolin and lecithin and also polyethoxylated or acetylated lanolin and lecithin derivatives, polyol fatty acid esters, monoglycerides and fatty acid alkanolamides, the latter simultaneously acting as foam stabilizers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, .alpha.-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carrageenan, gellan, pectines, or modified cellulose such as hydroxycellulose, hydroxypropylmethylcellulose. In addition polyacrylates or homopolymer of reticulated acrylic acids and polyacrylamides, carbomer (CARBOPOL types 980, 981, 1382, ETD 2001, ETD2020, ULTREZ 10) or SALCARE range such as SALCARE SC80 (steareth-10 allyl ether/acrylates copolymer), Salcare SC81 (acrylates copolymer), Salcare SC91 and Salcare AST (sodium acrylates copolymer/PPG-1 trideceth-6), SEPIGEL 305 (polyacrylamide/laureth-7), SIMULGEL NS and SIMULGEL EG (hydroxyethyl acrylate/sodium acryloyldimethyl taurate copolymer), STABILEN 30 (acrylates/vinyl isodecanoate crosspolymer), PEMULEN TR-1 (acrylates/C10-30 alkyl acrylate crosspolymer), LUVIGEL EM (sodium acrylates copolymer), ACULYN 28 (acrylates/beheneth-25 methacrylate copolymer), etc.

Polymers

As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatized cellulose ethers and silicones. Furthermore, the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, deoxyribonucleic acid, retinol, bisabolol, allantoin, phytantriol, panthenol, AHA acids, amino acids, ceramides, pseudoceramides, essential oils, plant extracts and vitamin complexes.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS(="Hindered Amine Light Stabilizers") compounds may also be mentioned.

Hydrotropic Agents

To improve the flow behaviour it is also possible to employ hydrotropic agents, for example ethoxylated or non-ethoxylated mono-alcohols, diols or polyols with a low number of carbon atoms or their ethers (e.g. ethanol, isopropanol, 1,2-dipropanediol, propylene glycol, glycerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo-A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent.

Colorants

There may be used as colorants the substances that are suitable and permitted for cosmetic purposes, as compiled, for example, in the publication "Kosmetische Farbemittel" of the Farbstoffkommission der Deutschen Forschungsgemeinschaft, Verlag Chemie, Weinheim, 1984, pages 81 to 106.

UV Screening Agents

Suitable sun screening agents would include a range of organic UV screening agents selected from the group consisting of 1(+/−)-1,7,7-trimethyl-3-[(4-methylphenyl)methylene]bicyclo-[2.2.1]heptan-2-one; p-methyl benzylidene camphor,1,7,7-trimethyl-3-(phenylmethylene)bicyclo [2.2.1]heptan-2-one; benzylidene camphor, (2-Hydroxy-4-methoxyphenyl)(4-methylphenyl)methanone, 2,4-dihydroxybenzophenone, 2,2',4,4'-tetrahydroxybenzophenone, 2-Hydroxy-4-methoxy benzophenone, 2-Hydroxy-4-methoxy benzophenone-5-sulfonic acid, 2,2'-dihydroxy-4, 4'-dimethoxybenzophenone, 2,2'-Dihydroxy-4-methoxybenzophenone, Alpha-(2-oxoborn-3-ylidene)toluene-4-sulphonic acid and its salts, 1-[4-(1,1-dimethylethyl) phenyl]-3-(4-methoxyphenyl)propane-1,3-dione, Methyl N,N,N-trimethyl-4-[(4,7,7-trimethyl-3-oxobicyclo[2,2,1]-hept-2-ylidene)methyl]anilinium sulphate, 3,3,5-Trimethyl cyclohexyl-2-hydroxy benzoate, Isopentyl p-methoxycinnamate, Menthyl-o-aminobenzoate,2-Ethylhexyl 2-cyano,3, 3-diphenylacrylate, 2-ethylhexyl 4-(dimethylamino)benzoate, 2-ethylhexyl 4-methoxycinnamate, 2-ethylhexyl salicylate, Benzoic acid,4,4',4"-(1,3,5-triazine-2,4,6-triyltriimino)tris-,tris(2-ethylhexyl)ester, 4-aminobenzoic acid, Benzoic acid, 4-amino-, ethyl ester, polymer with oxirane, 2-phenyl-1H-benzimidazole-5-sulphonic acid,2-Propenamide, N-[[4-[(4,7,7-trimethyl-3-oxobicyclo[2.2.1]hept-2-ylidene)methyl]phenyl]methyl]homopolymer. Triethanolamine salicylate, 3,3 '-(1,4-phenylenedimethylene)bis[7, 7-dimethyl-2-oxo-bicyclo[2,2,1]heptane-1 methanesulfonic acid], Titanium dioxide, 2,2'-Methylene-bis-[6-(2H-benzotriazol-2-yl)-4-(1,1,3,3-tetramethylbutyl)-phenol], Bi s-Ethylhexyloxyphenol Methoxyphenyl Triazine,1H-Benzimidazole-4,6-disulfonic acid, 2,2'-(1,4-phenylene)bis-, disodium salt, Benzoic acid, 4,4'-[[6-[[4-[[(1,1-dimethylethyl)amino] carbonyl]-phenyl]amino]1,3,5-triazine-2,4-diyl]diimino] bis-, Phenol, 2-(2H-benzotriazol-2-yl)-4-methyl-6-[2-methyl-3-[1,3,3,3-tetramethyl-1-[(trimethylsily)oxy] disiloxanyl]propyl]-,Dimethicodiethylbenzalmalonate, Benzenesulfonic acid, 3-(2H-benzotriazol-2-yl)-4-hydroxy-5-(1-methyl propyl)-, monosodium salt, Benzoic acid, 2-[4-(diethylamino)-2-hydroxybenzoyl]-, hexyl ester, 1-Dodecanaminium, N-[3-[[4-(dimethylamino)benzoyl]amino]-propyl]N,N-dimethyl-, salt with 4-methylbenzenesulfonic acid (1:1), 1-Propanaminium, N,N,N-trimethyl-3-[(1-oxo-3-phenyl-2-propenyl) amino]-, chloride, 1H-Benzimidazole-4, 6-disulfonic acid, 2,2'-(1,4-phenylene)bis-, 1,3,5-Triazine, 2,4,6-tris(4-methoxyphenyl)-, 1,3,5-Triazine, 2,4,6-tris[4-[(2-ethylhexyl)oxy]phenyl]1-Propanaminium, 3-[[3 [3-(2H-benzotriazol-2-yl)-5-(1,1-dimethylethyl)-4-hydroxyphenyl]-1-oxopropyl]amino]-N,N-diethyl-N-methyl-, methyl sulfate (salt), 2-Propenoic acid, 3-(1H-imidazol-4-yl)-, Benzoic acid, 2-hydroxy-, [4-(1-methylethyl)phenyl]methyl ester, 1,2,3-Propanetriol, 1-(4-aminobenzoate), Benzeneacetic acid, 3,4-dimethoxy-a-oxo-, 2-Propenoic acid, 2-cyano-3,3-diphenyl-, ethyl ester, Anthralinic acid, p-menth-3-yl ester, 2,2'-bis(1,4-phenylene)-1H-benzimidazole-4,6-disulphonic acid mono sodium salt or Disodium phenyl dibenzimidazole tetrasulfonate, 1,3,5-Triazine-2,4,6-triamine and N,N'-bis[4-[5-(1,1-dimethylpropyl)-2-benzoxazolyl]phenyl]-N"-(2-ethylhexyl).

Agents that Absorb UV Light and/or Provide Photo Protection to the Skin

Suitable agents that absorb UV light and/or provide photo protection to the skin, and/or optionally provide sunless tanning may include a compound of formula I:

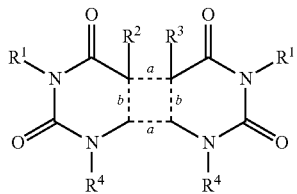

wherein:

each $R^1$ is independently H, $(C_1\text{-}C_6)$alkyl, $(C_3\text{-}C_7)$carbocycle or $R_aC(=O)-$, and the two $R^4$ groups together form a $-(C_3\text{-}C_8)$alkyl-group, a $-(C_2\text{-}C_6)$alkyl-Y-$(C_2\text{-}C_6)$alkyl-group or a $-(C_1\text{-}C_6)$alkyl-Y'-$(C_1\text{-}C_6)$alkyl-group; or each $R^4$ is independently H, $(C_1\text{-}C_6)$alkyl, $(C_3\text{-}C_7)$carbocycle or $R_aC(=O)-$, and the two $R^1$ groups together form a $-(C_3\text{-}C_8)$alkyl-group, a $-(C_2\text{-}C_6)$alkyl-Y-$(C_2\text{-}C_6)$alkyl-group or a $-(C_1\text{-}C_6)$alkyl-Y'-$(C_1\text{-}C_6)$alkyl-group; or the two $R^4$ groups together form a $-(C_3\text{-}C_8)$alkyl-group, a $-(C_2\text{-}C_6)$alkyl-Y-$(C_2\text{-}C_6)$alkyl group or a $-(C_1\text{-}C_6)$alkyl-Y'-$(C_1\text{-}C_6)$alkyl-group and the two $R^1$ groups together form a $-(C_3\text{-}C_8)$alkyl-group, a $-(C_2\text{-}C_6)$alkyl-Y-$(C_2\text{-}C_6)$alkyl-group or a $-(C_1\text{-}C_6)$alkyl-Y'-$(C_1\text{-}C_6)$alkyl-group;

the dashed bonds labeled "a" are absent and the dashed bonds labeled "b" are double bonds; or all the dashed bonds are single bonds;

$R^2$ is H, $(C_1\text{-}C_6)$alkyl or aryl, wherein aryl is optionally substituted with one or more $Z^1$ groups;

$R^3$ is H, $(C_1\text{-}C_6)$alkyl or aryl, wherein aryl is optionally substituted with one or more $Z^1$ groups;

Y is O, S, NH, NRC, P, P(=O) or POH;

Y' is $Si(R_b)_2$ or $-Si(R_b)_{2-0}-Si(R_b)_2-$;

each $R_a$ is independently $(C_1\text{-}C_6)$alkyl, $(C_3\text{-}C_7)$carbocycle or aryl, wherein aryl is optionally substituted with one or more $Z^1$ groups;

each $R_b$ is independently $(C_1\text{-}C_6)$alkyl, $(C_3\text{-}C_7)$carbocycle or aryl, wherein aryl is optionally substituted with one or more $Z^1$ groups;

each $R_c$ is independently $R_g$ or a $C_1\text{-}C_{18}$ saturated or unsaturated carbon chain that is optionally substituted with one or more groups independently selected from oxo (=O), hydroxy, mercapto, $(C_1\text{-}C_6)$alkoxy, $(C_1\text{-}C_6)$alkoxycarbonyl, $(C_1\text{-}C_6)$alkanoyloxy, $NR_dR_e$, carboxy, and aryl, wherein any aryl of $R_c$ is optionally substituted with one or more $R_f$;

each $R_d$ and $R_e$ is independently selected from H, $(C_1\text{-}C_6)$alkyl, $(C_1\text{-}C_6)$alkanoyl, phenyl, benzyl, and $R_g$;

each $R_f$ is independently selected from $(C_1\text{-}C_6)$alkyl, $(C_1\text{-}C_6)$alkoxy, $(C_1\text{-}C_6)$alkoxycarbonyl, $(C_1\text{-}C_6)$alkanoyloxy, $-C(=O)$-phenyl, and $-C(=O)CH_2C(=O)$-phenyl, wherein any phenyl is optionally substituted with one or more groups independently selected from $(C_1\text{-}C_6)$alkyl, $-SO_3H$, and $(C_1\text{-}C_6)$alkoxy;

each $R_g$ is

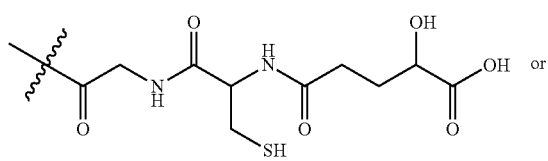

or

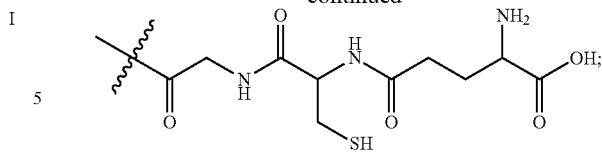

each $Z^1$ is independently selected from $(C_1\text{-}C_6)$alkyl, halogen, $-CN$, $-OR_{n1}$, $-NR_{g1}R_{r1}$, $-NR_{n1}COR_{p1}$, $-NR_{n1}CO_2R_{p1}$, $NO_2$, $-C(O)R_{n1}$, $-C(O)OR_{n1}$ and $-C(O)NR_{q1}R_{r1}$, wherein any $(C_1\text{-}C_6)$alkyl of $Z^1$ is optionally substituted with one or more (e.g. 1, 2, 3, 4, 5 or 6) halogen;

each $R_{n1}$ is independently selected from H and $(C_1\text{-}C_6)$alkyl, wherein any $(C_1\text{-}C_6)$alkyl of $R_{n1}$ is optionally substituted with one or more (e.g. 1, 2, 3, 4, 5 or 6) halogen;

each $R_{p1}$ is independently $(C_1\text{-}C_6)$alkyl; and $R_{q1}$ and $R_{r1}$ are each independently selected from H and $(C_1\text{-}C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;

or a salt thereof.

Specific groups of compounds and specific compounds of Formula I that may be incorporated in the topical composition described herein and methods of preparing such compounds are described in U.S. Pat. No. 9,403,778 and in U.S. Pat. No. 9,987,211, which are incorporated herein by reference in its entirety.

Suitable agents that absorb UV light and/or provide photo protection to the skin and/or optionally provide sunless tanning may include a compound of formula II:

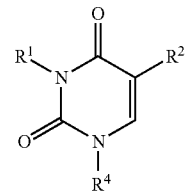

or a salt thereof, wherein:

$R^1$ is H, $(C_1\text{-}C_6)$alkyl, $(C_3\text{-}C_7)$carbocycle or $R_aC(=O)-$;

$R^2$ is H, $(C_1\text{-}C_6)$alkyl or aryl, wherein aryl is optionally substituted with one or more (e.g. 1, 2, 3, 4 or 5) $Z^1$ groups;

$R^4$ is H, $(C_1\text{-}C_{10})$alkyl, $(C_3\text{-}C_7)$carbocycle or $R_aC(=O)-$;

$R_a$ is or $(C_1\text{-}C_6)$alkyl, $(C_3\text{-}C_7)$carbocycle or aryl, wherein aryl is optionally substituted with one or more (e.g. 1, 2, 3, 4 or 5) $Z^1$ groups;

each $Z^1$ is independently selected from $(C_1\text{-}C_6)$alkyl, halogen, $-CN$, $-OR_{n1}$, $-NR_{g1}R_{r1}$, $-NR_{n1}COR_{p1}$, $-NR_{n1}CO_2R_{p1}$, $NO_2$, $-C(O)R_{n1}$, $-C(O)OR_{n1}$ and $-C(O)NR_{q1}R_{r1}$, wherein any $(C_1\text{-}C_6)$alkyl of $Z^1$ is optionally substituted with one or more (e.g. 1, 2, 3, 4, 5 or 6) halogen;

each $R_{n1}$ is independently selected from H and $(C_1\text{-}C_6)$alkyl, wherein any $(C_1\text{-}C_6)$alkyl of $R_{n1}$ is optionally substituted with one or more (e.g. 1, 2, 3, 4, 5 or 6) halogen;

each $R_{p1}$ is independently $(C_1\text{-}C_6)$alkyl; and $R_{q1}$ and $R_a$ are each independently selected from H and $(C_1\text{-}C_6)$ alkyl or $R_{q1}$ and $R_{n1}$ together with the nitrogen to which they are attached form a piperidine, pyrrolidine, morpholine, azetidine, thiomorpholine, piperazine or 4-methylpiperazine.

Specific groups of compounds and specific compounds of Formula II that may be incorporated in the topical composition described herein and methods of preparing such compounds are described in U.S. Pat. No. 9,987,211, which is incorporated herein by reference in its entirety.

Suitable agents that absorb UV light and/or provide photo protection to the skin may include a compound of formula III:

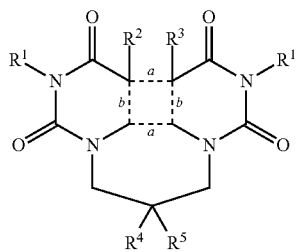

III wherein:
each $R^1$ is independently H, $(C_1-C_6)$alkyl, $(C_3-C_7)$carbocycle or $R_aC(=O)$; or the two $R^1$ groups together form a —$(C_3-C_8)$alkyl-group, a —$(C_2-C_6)$alkyl-Y—$(C_2-C_6)$alkyl-group or a —$(C_1-C_6)$alkyl-Y'—$(C_1-C_6)$alkyl-group; or the dashed bonds labeled "a" are absent and the dashed bonds labeled "b" are double bonds; or all the dashed bonds are single bonds;

$R^2$ is H, $(C_1-C_6)$alkyl or aryl, wherein aryl is optionally substituted with one or more (e.g. 1, 2, 3, 4 or 5) $Z^1$ groups;

$R^3$ is H, $(C_1-C_6)$alkyl or aryl, wherein aryl is optionally substituted with one or more (e.g. 1, 2, 3, 4 or 5) $Z^1$ groups;

$R^4$ is hydroxy, carboxy, $(C_1-C_6)$alkoxycarbonyl, —$OPO_3H_2$, —$OR_e$, or —$NR_dR_e$; and $R^5$ is H; or $R^4$ and $R^5$ taken together are oxo;

Y is O, S, NH, P, P(=O) or POH;

Y' is $Si(R_b)_2$ or —$Si(R_b)_2$—O—$Si(R_b)_2$—;

each $R_a$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;

each $R_b$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;

$R_c$ is $R_f$ or a $C_1-C_{20}$ saturated or $C_2-C_{20}$ unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein aryl is optionally substituted with one or more (e.g. 1, 2, 3, 4 or 5) $Z^1$ groups;

$R_d$ is H, $(C_1-C_6)$alkyl, or $(C_1-C_6)$alkanoyl;

$R_e$ is H or a $C_1-C_{20}$ saturated or $C_2-C_{20}$ unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein aryl is optionally substituted with one or more (e.g. 1, 2, 3, 4 or 5) $Z^1$ groups;

each $R_f$ is:

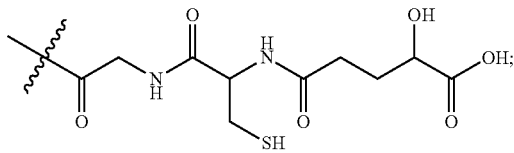 [SMILES: *C(=O)CNC(=O)C(CS)NC(=O)CCC(O)C(=O)O]

each $Z^1$ is independently selected from $(C_1-C_6)$alkyl, halogen, —CN, —$OR_{n1}$, —$NR_{g1}R_{r1}$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1-C_6)$alkyl of $Z^1$ is optionally substituted with one or more (e.g. 1, 2, 3, 4, 5 or 6) halogen;

each $R_{n1}$ is independently selected from H and $(C_1-C_6)$ alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl; and $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine; or a salt thereof.

Specific groups of compounds and specific compounds of Formula III that may be incorporated in the formulations described herein and methods of preparing such compounds are described in U.S. Pat. No. 9,364,406 and in U.S. Pat. No. 9,987,211, which are incorporated herein by reference in its entirety.

Sunscreening Agents

Formulations disclosed herein may include sun screening agents such as avobenzone, ecamsule, methyl anthranilate, oxybenzone, dioxybenzone, sulisobenzone, octinoxate, homosalate, octocrylene and octisalate. Such compositions may comprise organic UV filters, so-called hydrophilic or lipophilic sun-protection filters, which are effective in the UVA region and/or UVB region and (/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the WO93/04665. Further examples of organic filters are indicated in patent application EP-A 0 487 404. Particularly suitable for a combination are: para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed under the name "Uvinul P25" by BASF.

Other UV filter ingredients which may be incorporated in the topical compositions of the disclosure include:

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", "Uvinul N539" from BASF, Octocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronized form as an aqueous dispersion, for example marketed by BASF under the name "Tinosorb M".

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl 4'-aminobenzalmalonate)-s-triazine or 2,4,6-tris(biphenyl)-1,3,5-triazine. marketed as Tinosorb A2B by BASF, 2,2'-[6-(4-methoxyphenyl)-1,3,5-triazine-2,4-diyl]bis[5-(2-ethylhexyl)oxy]phenol, marketed as Tinosorb S by BASF, N2,N4-bis[4-[5-(1,1-dimethylpropyl)-2-benzoxazolyl]phenyl]-N-6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: Ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl) benzoxazol-2-yl(4-phenyl) imino]-6-(2-ethylhexyl)imino-1, 3,5-triazine, for example marketed by Sigma 3V under the name Uvasorb K2A, and mixtures comprising this.

Suitable organic UV-protecting substances can preferably be selected from: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15,1,1-Dicarboxy(2,2'-dimethylpropyl)-4,4-diphenylbutadiene, 2,4-bis[5-1 (dimethylpropyl)benzoxazol-2-yl(4-phenyl) imino]-6-(2-ethylhexyl)imino-1,3,5-triazine and mixtures thereof.

The compositions of the invention may comprise further inorganic UV filters, so-called particulate UV filters. These combinations with particulate UV filters are possible both as powder and also as dispersion or paste. In an embodiment the inorganic UV filter is a titanium dioxide, such as, for example, coated titanium dioxide (for example Eusolex® T-2000, Eusolex® T-AQUA, Eusolex® T-AVO, Eusolex® T-OLEO), a zinc oxide (for example Sachtotec), an iron oxide or a cerium oxide and/or zirconium oxide. Furthermore, combinations with pigmentary titanium dioxide or zinc oxide are also possible, where the particle size of these pigments are greater than or equal to 200 nm, for example Hombitan® FG or Hombitan® FFPharma.

Compositions of the invention may comprise inorganic UV filters which have been after treated by conventional methods, as described, for example, in Cosmetics & Toiletries, 1990, 105, 53-64. One or more of the following aftertreatment components can be: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

In an embodiment, particulate UV filters used in compositions of the invention are:
- untreated titanium dioxides, such as, the products Microtitanium Dioxide MT 500 B from Tayca; titanium dioxide P25 from Degussa,
- after treated micronized titanium dioxides with aluminium oxide and silicon dioxide aftertreatment, such as, the product "Microtitanium Dioxide MT 100 SA from Tayca; or the product "Tioveil Fin" from Uniqema,
- after treated micronized titanium dioxides with aluminium oxide and/or aluminium stearate/laurate aftertreatment, such as, Microtitanium Dioxide MT 100 T from Tayca, Eusolex T-2000 from Merck,
- after treated micronized titanium dioxides with iron oxide and/or iron stearate aftertreatment, such as, the product "Microtitanium Dioxide MT 100 F" from Tayca,
- after treated micronized titanium dioxides with silicon dioxide, aluminium oxide and silicone aftertreatment, such as, the product "Microtitanium Dioxide MT 100 SAS", from Tayca,
- after treated micronized titanium dioxides with sodium hexametaphosphates, such as, the product "Microtitanium Dioxide MT 150 W" from Tayca.

The treated micronized titanium dioxides employed for the combination may also be after treated with:
- octyltrimethoxysilanes; such as, the product Tego Sun T 805 from Evonik Goldschmidt GmbH,
- silicon dioxide; such as, for example, the product Parsol T-X from DSM,
- aluminium oxide and stearic acid; such as, the product UV-Titan M160 from Sachtleben,
- aluminium and glycerin; such as, the product UV-Titan from Sachtleben, aluminium and silicone oils, such as, the product UV-Titan M262 from Sachtleben,
sodium hexametaphosphate and polyvinylpyrrolidone,
polydimethylsiloxanes, such as, the product 70250 Cardre UF TiO2SI3" from Cardre,
polydimethylhydrogenosiloxanes, such as, for example, the product Microtitanium Dioxide USP Grade Hydrophobic" from Color Techniques.

In a particular embodiment, compositions of the invention may include untreated zinc oxides, such as, the product Z-Cote from BASF (Sunsmart), Nanox from Elementis. In another particular embodiment, compositions of the invention may include after treated zinc oxides, such as, the following products:

"Zinc Oxide CS-5" from Toshibi (ZnO after treated with polymethylhydrogeno-siloxanes);
Nanogard Zinc Oxide FN from Nanophase Technologies;
"SPD-Z1" from Shin-Etsu (ZnO after treated with a silicone-grafted acrylic polymer, dispersed in cyclodimethylsiloxanes;
"Escalol Z100" from ISP (aluminium oxide-after treated ZnO dispersed in an ethylhexyl methoxycinnamate/PVP-hexadecene/methicone copolymer mixture); and
"Fuji ZNO-SMS-10" from Fuji Pigment (ZnO after treated with silicon dioxide and polymethylsilesquioxane).

In another particular embodiment, compositions of the invention may include untreated cerium oxide micropigment, for example with the name "Colloidal Cerium Oxide" from Rhone Poulenc. In another particular embodiment, compositions of the invention may include untreated and/or after treated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, mixtures of aluminium oxide, silicon dioxide and silicone-after treated titanium dioxide, zinc oxide mixtures, such as, the product UV-Titan M261 from Sachtleben, can also be used in combination with the UV protection agents according to the invention.

Methods of Use

In some embodiments, the present disclosure is directed to a method of treating a skin of a subject for effects of radical-induced damage. Radical-induced damage may encompass damage from free radicals from sunlight (UVB, UVA, Visible Light), HEV (blue) light, Infrared (IR), pollution, irritants, allergens, or various environmental toxins that are destructive to the skin, for example, by hydrolyzing elastin fibers in the skin or desynthesizing collagen in the lower dermal layers of the skin. Exemplary radical-induced damage that may be treated, prevented, minimized, reduced, or attenuated after administering to a skin of a subject an effective amount of any of the topical compositions described herein includes, without limitations, severity of photodamage, lack of tactile smoothness, back of visual smoothness, lack of softness, lack of luminosity, lack of radiance, skin texture, skin wrinkles, fine facial wrinkles, crow's feet, dyschromia, crepey skin texture, appearance of fine lines, skin roughness, skin sagging, skin firmness, reduction in skin elasticity, age spots, hyperpigmentation, scars, skin surface irregularities, rosacea, acne, psoriasis, reduction in the skin's regenerative and renewal process, weather-beaten appearance, yellowing, redness, dryness, ichthyosis, and other damaging skin conditions.

In certain embodiments, the present disclosure is directed to a method of treating a skin of a subject by administering to the skin of a subject an effective amount of any of the formulations described herein, wherein the skin exhibits improved tactile smoothness after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved softness after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved luminosity after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved radiance after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved visual smoothness after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved firmness after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved skin texture after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved overall photo-aging appearance after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits reduced dryness after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin demonstrates reduced barrier damage (e.g., as exhibited by a lower transepidermal water loss increase) after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein, as compared to the transepidermal water loss increase exhibited by administration of a comparative formulation. While some transepidermal water loss (TEWL) increase may be anticipated with retinoid based treatment, in certain embodiments, the TEWL increase exhibited by a skin treated with any of the formulations described herein at a given time point of treatment (e.g., about 4 weeks, about 8 weeks, about 12 weeks, etc) may be less than about 100%, less than about 95%, less than about 90%, or less than about 88%. The TEWL increase may be measured as compared to a baseline measurement taken at time zero before initiation of treatment.

In certain embodiments, the present disclosure is directed to a method of treating a skin of a subject by administering to the skin of a subject an effective amount of any of the formulations described herein, wherein the skin exhibits improved crow's feet after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improved dyschromia after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improvement in one or more of: tactile smoothness, softness, luminocity, radiance, visual smoothness, firmness, skin texture, overall photo-aging appearance, dryness, crow's feet, or dyschromia after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein, and wherein the subject experiences enhanced tolerability (e.g., in terms of one or more of itching, stinging, burning, redness, or swelling) as compared to a comparably efficacious tretinoin formulation. A comparably efficacious tretinoin formulation being a formulation that exhibits a similar improvement (i.e., without statistically significant difference, as defined in the clinical study described in the examples) in one or more of: tactile smoothness, softness, luminocity, radiance, visual smoothness, firmness, skin texture, overall photo-aging appearance, dryness, crow's feet, or dyschromia after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin exhibits improvement in one or more of: tactile smoothness, softness, luminocity, radiance, visual smoothness, firmness, skin texture, overall photo-aging appearance, dryness, crow's feet, or dyschromia after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein, and wherein the subject experiences reduced barrier damage (e.g., in terms of transepidermal water loss) as compared to a comparably efficacious tretinoin formulation. A comparably efficacious tretinoin formulation being a formulation that exhibits a similar improvement (i.e., without statistically significant difference, as defined in the clinical study described in the examples) in one or more of: tactile smoothness, softness, luminocity, radiance, visual smoothness, firmness, skin texture, overall photo-aging appearance, dryness, crow's feet, or dyschromia after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin demonstrates newly formed collagen after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiments, the present disclosure is directed to a method of treating a skin of a subject by administering to the skin of a subject an effective amount of any of the formulations described herein, wherein the skin demonstrates epidermal thickening after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein. The epidermal thickening at a given time point of treatment (e.g., about 4 weeks, about 8 weeks, about 12 weeks, etc) may range from any of about 10%, about 20%, about 30%, or about 40% to any of about 50%, about 60%, about 70%, about 80%, about 90%, about 100%, about 150%, or about 200% as compared to baseline (e.g., at time zero which is before initiation of treatment). In certain embodiments, the epidermal thickening at a given time point of treatment (e.g., about 4 weeks, about 8 weeks, about 12 weeks, etc) may be at least about 10%, at least about 20%, at least about 30%, at least about 40%, or at least about 50%.

In certain embodiments, the present disclosure is directed to a method of treating a skin of a subject by administering to the skin of a subject an effective amount of any of the formulations described herein, wherein the skin demonstrates greater epidermal thickening after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein as compared to a comparably efficacious tretinoin formulation. A comparably efficacious tretinoin formulation being a formulation that exhibits a similar improvement (i.e., without statistically significant difference, as defined in the clinical study described in the examples) in one or more of: tactile smoothness, softness, luminocity, radiance, visual smoothness, firmness, skin texture, overall photo-aging appearance, dryness, crow's feet, or dyschromia after administration of the formulations for a duration of about 1 week to about 16 weeks, about 2 weeks to about 14 weeks, about 4 weeks to about 12 weeks, about 4 weeks, about 8 weeks, about 12 weeks, or any single value or sub-range therein.

In certain embodiment, the present disclosure is directed to a treatment regimen method that includes administering to a skin of a subject that has been subjected or will be subjected to a dermatological procedure an effective amount of any of the formulations described herein. In certain embodiments, the methods described herein further include performing the dermatological procedure after administration of the topical composition and/or before administration of the topical composition, depending on the treatment regimen. In certain embodiments, the topical compositions described herein is helpful in improving the outcomes of dermatological procedures, e.g., by speeding healing, quelling discomfort, quenching reactive oxygen species (ROS), inducing collagen formation, or any combination thereof.

The effective amount will vary with the particular condition or conditions being treated, the severity of the condition, the duration of the treatment, the specific components of the formulation being used, and other factors. In certain embodiments, the formulations described herein are suitable for administration by frequent periodic application, such as by a once, twice, thrice or four times daily application or more, e.g., for a duration of at least 1 day, at least 3 days, at least 5 days, at least 7 days, at least 10 days, at least 14 days, at least 21 days, at least 30 days, at least 8 weeks, at least 12 weeks, and so on. Accordingly, in certain embodiments, the methods described herein further include periodically repeating the administration of the formulation.

In certain embodiments, the formulations described herein are suitable for a pre or post procedure administration, such as before or after a dermatological procedure.

Method of Preparation

The instant disclosure is also directed to a method of preparing any of the formulations described herein. Formulations and delivery systems of the present disclosure may be prepared under ambient conditions. In certain embodiments, formulations of the present disclosure are prepared under an inert atmosphere. In particular aspect of this embodiment, the inert atmosphere is an inert gas, such as but not limited to, nitrogen, argon, or combinations thereof. In certain embodiments, formulations of the present disclosure are prepared under a dry inert atmosphere, which may comprise, consist essentially of, or consist of one or more dry inert gases, including but not limited to dry nitrogen, dry argon, or a combination thereof. In certain embodiments, the preparing the formulation under any of the dry inert atmospheres described herein stabilizes the formulation so that certain ingredients (e.g., retinol) do not separate and/or precipitate out.

In certain embodiments, the method for preparing formulations described herein comprises a process with a plurality of steps in which the steps may be precisely broken up and/or associated with corresponding conditions (e.g., temperature, mixing intensity, and duration) to solubilize the various ingredients, stabilize the final formulation, and reduce and/or minimize and/or eliminate precipitation.

For example, a first amount of isopentyldiol (or another suitable polyol as described herein) may be combined with a first amount polysorbate 80 (or another suitable surfactant as described herein) and with xanthine, such as caffeine, to form a first mixture. The first mixture may be mixed, e.g., with a propeller mixer, for a first duration (e.g., about 15 minutes to about 90 minutes, about 30 minutes to about 60 minutes, or about 40 minutes to about 50 minutes) at a first temperature (e.g., about 60° C. to about 120° C., about 70° C. to about 110° C., or about 80° C. to about 100° C.) until the xanthine (e.g., caffeine) is dissolved and the first mixture is clear and lump free. Thereafter, in certain embodiments, the first mixture may be cooled to a second temperature (e.g., about 50° C. to about 110° C., about 60° C. to about 100° C., or about 70° C. to about 90° C.).

In certain embodiments, a first amount of DMI and/or a first amount of ethoxydiglycol may be added into the first mixture one at a time to ultimately form a second mixture. After addition of each ingredient, the mixture may be mixed for a second duration (e.g., about 1 minute to about 30 minutes, about 5 minutes to about 25 minutes, or about 10 minutes to about 20 minutes) until the second mixture is uniform and lump free. Thereafter, in certain embodiments, the second mixture may be cooled to a third temperature (e.g., about 30° C. to about 90° C., about 40° C. to about 80° C., or about 50° C. to about 70° C.).

In certain embodiments, in a first separate vessel, a second amount of isopentyldiol (or another suitable polyol as described herein) may be combined with *Camellia sinensis* (green tea) polyphenols to form a third mixture. In certain embodiments, the diol is used to solubilize the *Camellia sinensis* (green tea) polyphenols, by, e.g., forming a complex between the diol and the *Camellia sinensis* (green tea) polyphenols. The third mixture may be mixed for a third duration until the third mixture is uniform and lump free. Thereafter, in certain embodiments, the third mixture may be heated to the third temperature (e.g., about 30° C. to about 90° C., about 40° C. to about 80° C., or about 50° C. to about 70° C.) to be substantially similar to the third temperature of the cooled second mixture. In certain embodiments, upon heating the third mixture, it may become clear. In certain embodiments, the *Camellia sinensis* (green tea) polyphenols are not added directly into the second mixture, but instead are first solubilized in a separate vessel, to more effectively solubilize the *Camellia sinensis* (green tea) polyphenols.

In certain embodiments, the third mixture may be added to the second mixture to form a fourth mixture.

In certain embodiments, in a second separate vessel, retinol (which may be complexed and/or co-solubilized with Polysorbate 20) may be combined, in a concentrated form, with a plurality of ingredients from the fourth mixture, such as, with a second amount of polysorbate 80, a second amount of DMI, and a second amount ethoxydiglycol to form a fifth mixture. In this manner, it is believed, without being construed as limiting, that by introducing the retinol to a plurality of ingredients in the formulation, it will remain stable in the formulation and will not precipitate out. The fifth mixture may be mixed until it is uniform, lump free, and clear.

In certain embodiments, the fifth mixture may be added to the fourth mixture to form a sixth mixture at a fourth temperature (e.g., about 30° C. to about 70° C., about 40° C. to about 60° C., or about 45° C. to about 55° C.).

In certain embodiments, bakuchiol and/or additional antioxidants (e.g., black tea extract and/or licorice root extract) may be added into the sixth mixture one at a time to ultimately form the final formulation. After addition of each ingredient, the mixture may be mixed for a duration (e.g., about 1 minute to about 15 minutes, about 3 minutes to about 10 minutes, or about 4 minutes to about 6 minutes) until the final formulation is uniform and lump free. Thereafter, in certain embodiments, the final formulation may be cooled to a final temperature (e.g., about 10° C. to about 50° C., about 20° C. to about 40° C., or about 25° C. to about 30° C.).

As can be seen from the procedure described hereinabove, in certain embodiments, certain ingredients of the formulation are solubilized separately or are added in two separate steps (e.g., a first amount at a certain step and a second amount at a different step) to arrive at a uniform, lump free, and stable formulation. In certain embodiments, the procedure is done under controlled conditions to minimize or eliminate introduction of water, air, oxygen, or light into the process so as to maintain the stability of the various ingredients (e.g., retinol and *Camellia sinensis* (green tea) polyphenols to name a few).

ILLUSTRATIVE EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

The skincare formulations were tested in clinical study using exemplary formulations of retinol at 0.25%, 0.5% and 1.0% where one cohort of users started out using the disclosed formulations containing all-trans retinol in those dosages, starting out at the lowest dosage and stepping up to the next highest dosage after one month of use each time. A second group did the same with tretinoin, a prescription retinoid considered the gold standard in anti-aging retinoid treatment. Participants stepped up monthly (0.025%, 0.05% and 0.1%) and the group using the retinol formulations disclosed herein in the examples below experienced excellent, surprising results, as good or better in many cases than individuals in the group using tretinoin, and with less irritation.

The data obtained demonstrate the effectiveness of the disclosed topical retinoid containing formulations for improvement in skin properties.

The disclosed formulations may be used in a step-up program as described above or alone and/or with adjunct products, for example a sunscreen, moisturizer and cleanser.

In exemplary embodiments of the formulations disclosed herein, the ingredients are: Isopentyldiol, Dimethyl Isosorbide, Polysorbate 80, Ethoxydiglycol, Caffeine, *Camellia Sinensis* (Green Tea) Polyphenols, Retinol, Polysorbate 20, Bakuchiol, Purified Water, *Glycyrrhiza Glabra* (Licorice) Root Extract, *Camellia Sinensis* (Black Tea) Leaf Extract, Glycerin.

In the disclosed formulations, ethoxydiglycol is used in a customary way and in accordance with the European Union cosmetic regulations requiring it to be present at less than 2.6%. Isopentyldiol, Dimethyl Isosorbide, Polysorbate 80 are comparatively much weaker, gentler solvents for retinol and retinol derivatives (retinoids).

The formulations of the present disclosure provide skincare treatments with results comparable to a prescription retinoid and stay within the cosmetic (non-drug) dosing of retinol so that the formulations may be used without restriction.

Exemplary Compositions (all expressed as % w/w)

Example 1

| Ingredient | Concentration (wt %) |
| --- | --- |
| Isopentyldiol | 10-90% |
| Polysorbate 80 | 1-40% |
| Caffeine | 0.01-10% |
| Dimethyl Isosorbide | 5-90% |
| Ethoxydiglycol | 0-80% |
| Green Tea Polyphenols | 0.1-15% |
| Retinol | 0.01-30% |
| Polysorbate 20 | 0-30% |
| Bakuchiol | 0-20% |
| Black Tea Extract | 0-20% |
| Licorice Extract | 0-20% |

Example 2

| Ingredient | Concentration (wt %) |
| --- | --- |
| Isopentyldiol | 45-65% |
| Polysorbate 80 | 6-10% |
| Caffeine | 0.5-2.5% |
| Dimethyl Isosorbide | 20-40% |
| Ethoxydiglycol | 1-5% |
| Green Tea Polyphenols | 01-5% |
| Retinol | 0.05-1.5% |
| Polysorbate 20 | 0.05-2% |
| Bakuchiol | 0.1-3.0% |
| Black Tea Extract | 0.001-5% |
| Licorice Extract | 0.001-5% |

Example 3: 0.25% Retinol

| Ingredient | Concentration (wt %) |
| --- | --- |
| Isopentyldiol | QS to 100% |
| Polysorbate 80 | 8.52% |
| Caffeine | 1.25% |
| Dimethyl Isosorbide | 30.00% |
| Ethoxydiglycol | 2.50% |
| Green Tea Polyphenols | 1.25% |
| Retinol | 0.25% |
| Polysorbate 20 | 0.25% |
| Bakuchiol | 1.00% |
| Black Tea Extract | 0.001% |
| Licorice Extract | 0.001% |

Example 4: 0.5% Retinol

| Ingredient | Concentration (wt %) |
| --- | --- |
| Isopentyldiol | QS to 100% |
| Polysorbate 80 | 8.52% |
| Caffeine | 1.25% |
| Dimethyl Isosorbide | 30.00% |
| Ethoxydiglycol | 2.50% |
| Green Tea Polyphenols | 1.25% |
| Retinol | 0.50% |
| Polysorbate 20 | 0.50% |
| Bakuchiol | 1.00% |
| Black Tea Extract | 0.001% |
| Licorice Extract | 0.001% |

Example 5: 1.0% Retinol

| Ingredient | Concentration (wt %) |
| --- | --- |
| Isopentyldiol | QS to 100% |
| Polysorbate 80 | 8.52% |
| Caffeine | 1.25% |
| Dimethyl Isosorbide | 30.00% |
| Ethoxydiglycol | 2.50% |
| Green Tea Polyphenols | 1.25% |
| Retinol | 1.00% |
| Polysorbate 20 | 1.00% |
| Bakuchiol | 1.00% |
| Black Tea Extract | 0.001% |
| Licorice Extract | 0.001% |

Clinical Study

Method

A single-site, double-blind controlled comparative study enrolled 45 photoaged females ages 35-65, Fitzpatrick skin types I-IV, with moderate wrinkling. Subjects who used facial retinoids within 3 months of screening, and/or facial alpha-hydroxy acids within 1 month were excluded. Subjects were randomized 2:1 into the following groups:

Cell 1: 30 subjects applied 0.25% retinal serum (e.g., composition of Example 3 above) for 4 weeks. The 0.25% retinal serum was used twice weekly for week 1, then every other night for week 2, then every night for weeks 3 and 4. The Test Moisturizer (Lipid Replenishing Cream, TOPIX Pharmaceuticals, Inc, Amityville, NY) was placed on top of the retinal serum at each nightly application and every morning.

Cell 2: 15 subjects applied 0.025% tretinoin cream for 4 weeks. The 0.025% tretinoin cream was used twice weekly for the week 1, then every other night for week 2, then every night for weeks 3 and 4. Test Moisturizing cream (CeraVe Moisturizing Cream, L'Oreal, NY) was placed on top of the tretinoin cream (Ortho Dermatologies, NJ) at each application and every morning.

The dermatologist-investigator and subjects assessed the following facial efficacy parameters: overall severity of photodamage, dryness, lack of tactile smoothness, lack of visual smoothness, lack of softness, lack of luminosity, lack of radiance, lack of firmness, poor skin texture, fine facial wrinkles, crow's feet, dyschromia, and crepey cheek skin texture. All assessments were graded on a 5-point ordinal scale (0=none, 1=minimal, 2=mild, 3=moderate, 4=severe). In addition, the investigator and the subjects assessed overall clinical improvement from baseline at week 12, using a 5-point scale (1=much improved, 2=moderately improved, 3=slightly improved, 4=no change, 5=worse). The investigator and subjects referred to baseline images (front, right and left side images) of the subjects in completing this evaluation.

Tolerability was graded in terms of the following parameters: itching, stinging, burning, redness, swelling. All assessments were made on a 5-point ordinal scale (0=none, 1=minimal, 2=mild, 3=moderate, 4=severe).

Compliance was reinforced using weekly diary sheets and subjects were asked to record product application and any comments on the provided weekly diary. A compliance text was sent at week 2 to ask subjects to contact the research center if they were experiencing any difficulties with the study products and to encourage subjects to be consistent with treatments and continue to maintain daily diaries.

Clinical photography was captured at each office visit using visible light of the central, right, and left face with a VISIA CR43 camera system (Canfield Scientific, NJ). Non-invasive assessments for barrier function in the form of transepidermal water loss (TEWL) measurements were taken from the left face using Evaporimeter, Cyberderm, Broomall, PA Skin biopsies were obtained from 6 subjects in cell 1 and 4 subjects in cell 2. The 2 mm skin biopsies were taken from the face anterior to the right ear at baseline (visit 1) and from the face anterior to the left ear at week 12 (visit 4). Histologic evaluation included evaluation for epidermal plumping, stratum corneum compaction, increased collagen, increased glycosaminoglycans (GAG), decreased melanin, improved vascularity and reteridges, and decreased solar elastosis. These analyses were conducted on formalin fixed specimens utilizing H&E, elastic stains, and GAG stains (Garron Solomon, Tri point Diagnostics, Morrisville, NC).

Statistics

Along with descriptive statistics (means, standard deviations, and percentages), investigator ordinal nonparametric data was analyzed using the Wilcoxon signed rank test and sign test for paired comparison at different time points within and between groups. Change was considered significant at a p-value of less than or equal to 0.05.

Results

Forty-three of forty-five subjects successfully completed the study. Two of forty-five subjects discontinued due to retinoid tolerability issues, one from each study cell. This was expected as the study involved a fairly aggressive retinization protocol. All facial irritation resolved immediately after retinoid discontinuation. Several adverse experiences (6 in Cell 1,4 in Cell 2) occurred as a result of the rapid facial retinization. These were expected to occur, and all resolved with changes to the facial treatment regimen. No serious adverse events occurred during the conduct of the study.

Retinol Experience

All subjects were asked to rate their experience at the end of the 12-week study. A lower score was indicative of a superior performance. The ancillary lipid replenishing cream used in the retinal serum group was rated statistically superior to the currently marketed cream used in the tretinoin group (P=0.038). Subjects in both groups reported improvements in self-confidence, beautiful skin, and empowerment.

Investigator Efficacy

The investigator graded facial skin appearance parameters using a 5-point ordinal scale (0=none, 1=minimal, 2=mild, 3=moderate, 4=severe) at baseline (visit 1), week 4 (visit 2), and week 8 (visit 3), and week 12 (visit 4). There were no statistically significant attributes at any time point between the two groups indicating parity between retinol serum and tretinoin according to investigator assessed efficacy.

Figure 2:
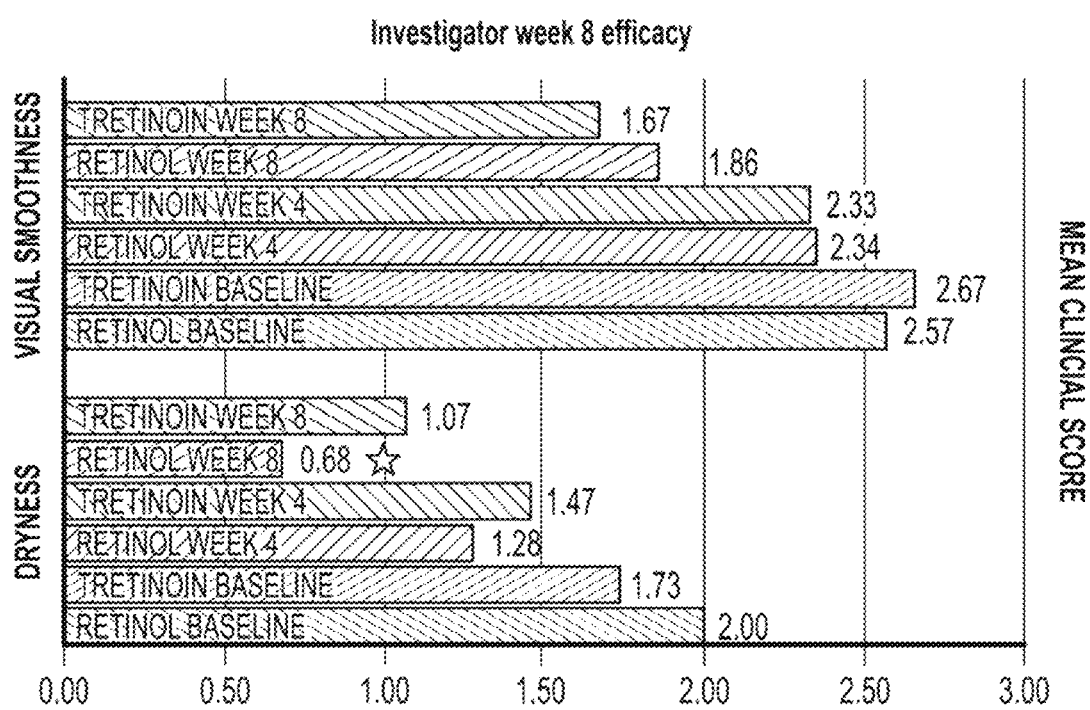
FIG. 2 illustrates an investigator week 8 efficacy chart in terms of mean clinical scores for dryness and visual smoothness of skin treated with a formulation according to certain embodiments described herein as compared to a comparative tretinoin formulation.

The longitudinal intragroup assessment demonstrated that after 4 weeks of use, there was statistically significant improvement in tactile smoothness, softness, luminosity, and radiance for both groups, but the significance was higher for the retinol group (FIG. 1). In addition, there was statistically significant improvement in visual smoothness with retinol ($P=0.031$), however no significance was seen with tretinoin. Improvement continued into week 8 with both groups showing statistical significance in tactile smoothness, visual smoothness, softness, luminosity, radiance, firmness, skin texture, and overall photoaging appearance. There was a highly statistically significant improvement noted in skin dryness ($P<0.001$) with the retinol that was not seen with the tretinoin (FIG. 2). After 12 weeks of use, both products demonstrated improvement parity, although the statistical significance continued to be higher for the retinol group.

Investigator Overall Efficacy

At week 12, the investigator graded overall improvement in facial appearance using the following scale: 1=much improved, 2=moderately improved, 3=slightly improved, 4=no change, 5=worse. There was no statistically significant difference ($P=0.778$) between retinol serum and tretinoin overall improvement.

Investigator Tolerability

The investigator assessed tolerability by querying the subjects on itching, stinging, and burning while evaluating redness and swelling. There were no statistically significant differences between the retinol serum and the tretinoin in any of the tolerability categories.

Subject Efficacy

Subjects assessed their skin appearance across various photodamage parameters using a 5-pointordinal scale (0=none, 1=minimal, 2=mild, 3=moderate, 4=severe) at baseline, week 4, week 8, and week 12. There were no statistically significant differences between the groups at any time except for better visual smoothness seen with the retinol serum at week 8 ($P=0.045$, FIG. 3).

Figure 3:
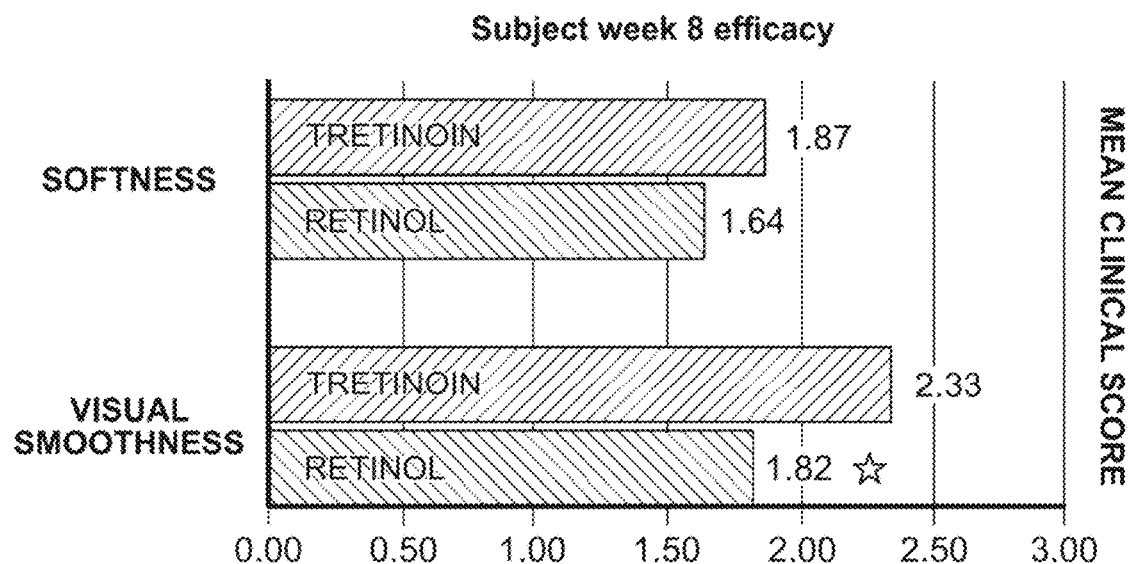
FIG. 3 illustrates a subject week 8 efficacy chart in terms of mean clinical scores for dryness and visual smoothness of skin treated with a formulation according to certain embodiments described herein as compared to a comparative tretinoin formulation.
Figure 4:
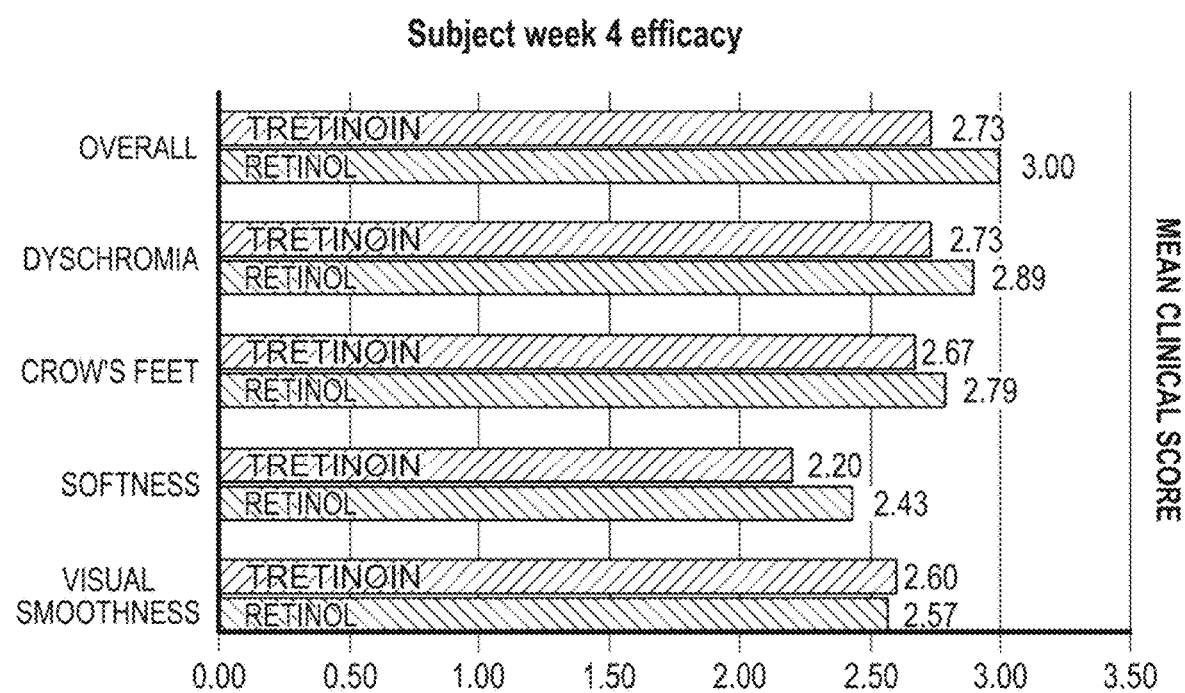
FIG. 4 illustrates a subject week 4 efficacy chart in terms of mean clinical scores for overall appearance, dyschromia, crow's feet, softness, and visual smoothness of skin treated with a formulation according to certain embodiments described herein as compared to a comparative tretinoin formulation.

Intragroup longitudinal assessment analysis indicated that both retinol serum and tretinoin users experienced improvement, however, there was higher statistical significance across all time points seen with retinol serum users. Specifically, statistically significant improvement was observed for subject assessed visual smoothness ($P=0.003$), softness ($P=0.006$), crow's feet ($P=0.001$), dyschromia ($P=0.004$), and overall photoaged appearance ($P=0.031$) with the retinol at week 4 (FIG. 4). Softness continued to be significant for the retinol serum group at week 8 ($P<0.001$) and not for the tretinoin group (FIG. 3). Both treatments demonstrated statistical significance for most parameters at week 12.

Subject Overall Efficacy

After 12 weeks of use, subjects assessed their overall clinical improvement from baseline, using a 5-point scale (1=much improved, 2=moderately improved, 3=slightly improved, 4=no change, 5=worse). The subjects referred to their baseline images to make the assessment. No statistical difference was noted between the two groups ($P=0.697$). Both retinol serum and tretinoin users on average reported much-improved skin.

Subject Tolerability

Figure 5:
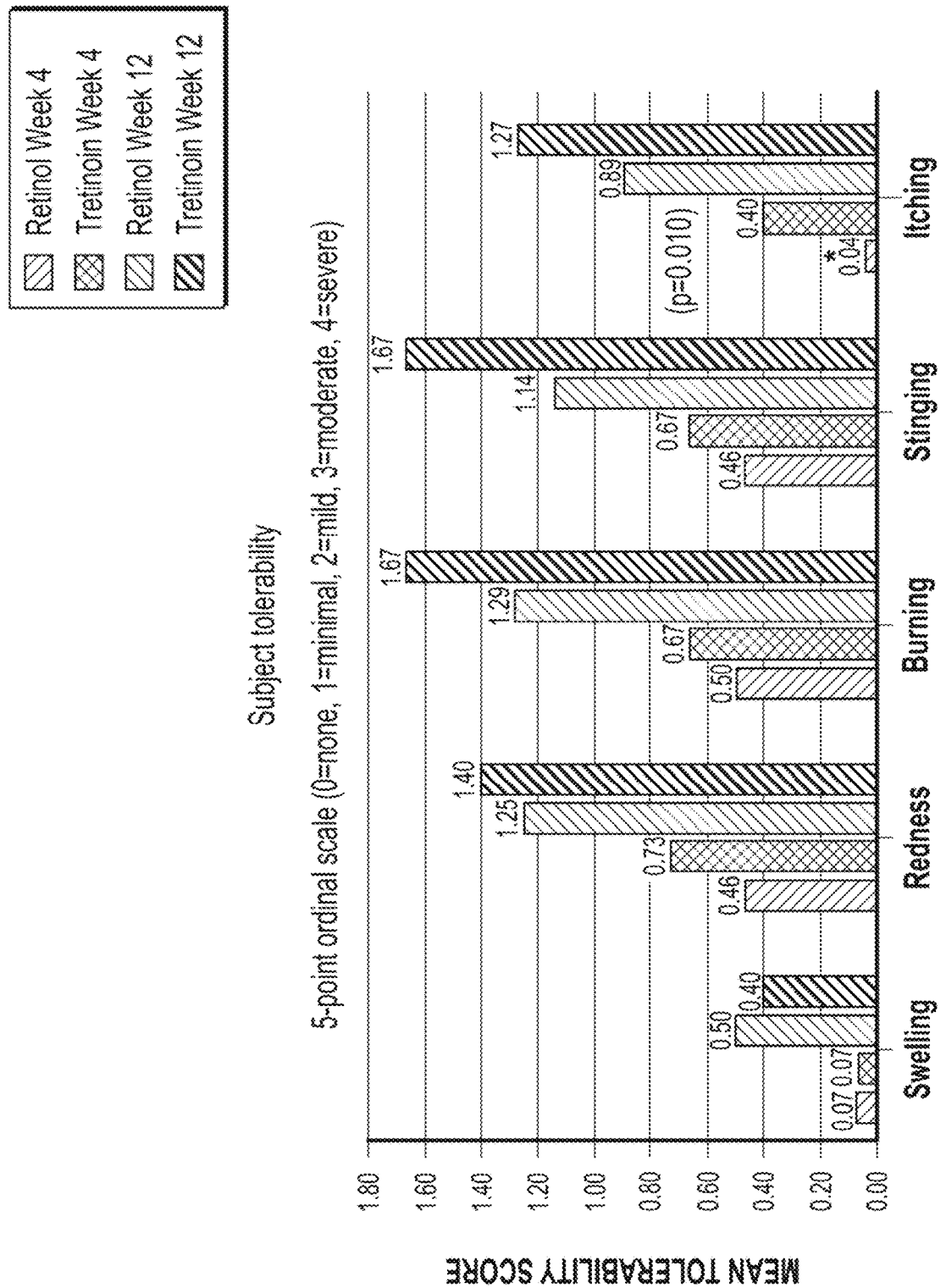
FIG. 5 illustrates a subject mean tolerability score chart on weeks 4 and 12 in terms of mean tolerability scores for swelling, redness, burning, stinging, and itching of a skin treated with a formulation according to certain embodiments described herein as compared to a comparative tretinoin formulation.

The subjects rated tolerability in terms of itching, stinging, burning, redness, and swelling with a lower rating indicating less tolerability issues. There was only one statistically significant difference between retinol serum and tretinoin users in terms of itching at week 4. The retinol serum group experienced less itching ($P=0.010$; FIG. 5).

Transepidermal Water Loss (TEWL)

TEWL (Evaporimeter, Cyberderm, Broomall, PA) measurements were taken at baseline, week 8, and week 12. While TEWL increased with both the retinol and tretinoin as expected, no statistically significant difference was observed between both groups at 8 weeks ($P=0.337$) or 12 weeks ($P=0.604$). While both products induced barrier damage ($P<0.001$) consistent with retinoid use, the longitudinal intragroup comparison showed less barrier damage at week 12 with retinol serum than tretinoin treatment. At week 12, there was a 104% increase in TEWL with the tretinoin and an 88% increase with the retinol serum. TEWL increase was 16% lower in the retinol group as compared to the tretinoin group.

Histology

The baseline histology was compared to the week 12 histology. After 12 weeks of use, retinol serum subjects demonstrated newly formed collagen and greater epidermal thickening compared to tretinoin-treated subjects.

FIGS. 6A-6D illustrated epidermal thickening ranging about 30% to about 50% increase as compared to baseline. FIGS. 6A-6D illustrated collagen deposition to be about two to three times as much compared to the baseline (initial and week 12, same subject, retinol group).

Figure 6A:
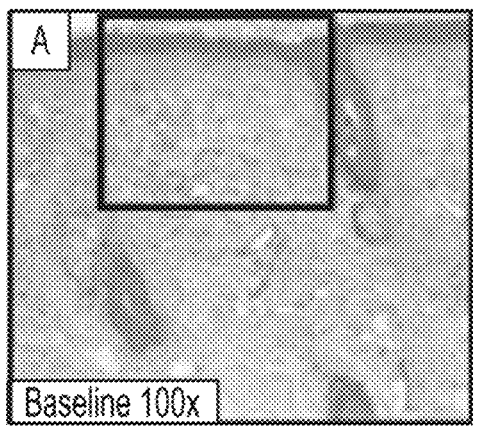
FIGS. 6A-6D illustrate histology of a skin treated with a formulation according to certain embodiments described herein on week 12 (FIGS. 6B and 6D) as compared to baseline (FIGS. 6A and 6C).
Figure 6B:
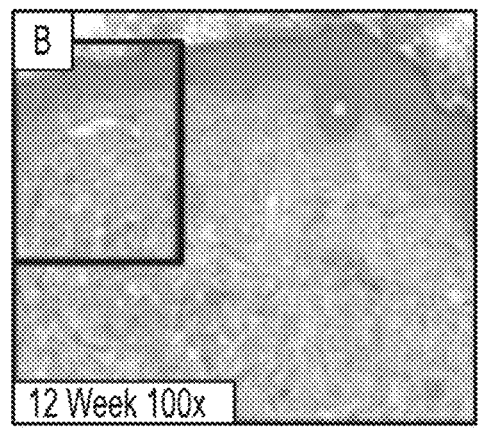
Figure 6C:
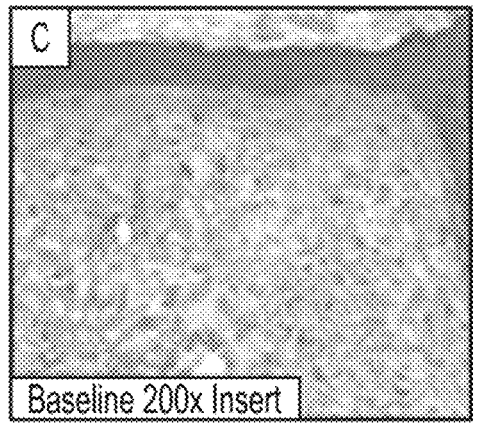
Figure 6D:
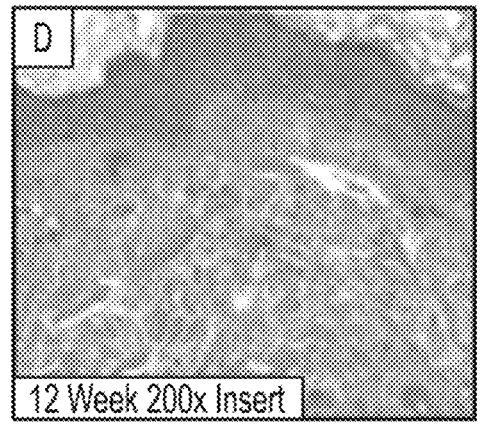

FIG. 6A being depictive of 100× magnification of a baseline sample and FIG. 6C being depictive of a 200× magnification of the baseline sample. FIG. 6B being depictive of a 100× magnification of a 12 week sample and FIG. 6D being a 200× magnification of the 12 week sample.

DISCUSSION

After 12 weeks of use, both retinol serum and tretinoin demonstrated parity across many investigator and subject assessment endpoints, although on average, the significance was higher for the retinol serum group. The skin appeared smoother and less dry at the earliest evaluation visit, 4 weeks after beginning treatment for subjects in the retinol serum group. Retinol serum subjects reported several areas of facial improvement following 4 weeks of application including smoother looking skin, softer skin, a reduced appearance of fine lines and wrinkles around the eyes, improved evenness of skin tone, and an overall reduction in photodamage. Retinol subject improvements in skin softness continued into week 8, whereas skin softness improvement was not seen until week 8 for the tretinoin subjects.

The TEWL measurement means suggested 16% less water loss through a damaged barrier in subjects using retinol serum for the study duration. The presence of newly formed collagen and greater epidermal thickening also coincided with clinical and functional improvements by study completion.

CONCLUSION

Retinal serum with bakuchiol represents an efficacious alternative to prescription tretinoin, providing rapid retinization and appearance improvement in photodamaged skin.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

Reference throughout this specification to numerical ranges should not be construed as limiting and should be understood as encompassing the outer limits of the range as well as each number and/or narrower range within the enumerated numerical range.

The term "about", when referring to a physical quantity, is to be understood to include measurement errors within, and inclusive of 10%. For example, "about 100° C." should be understood to mean "100±10° C.".

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method for therapeutic treatment of a dermatological condition, comprising topically applying to an affected area a therapeutically effective amount of a topical formulation comprising a skin treatment active agent comprising retinol and an activation solvent system comprising isopentyldiol, ethoxydiglycol, dimethyl isosorbide, and a non-ionic surfactant, wherein the topical formulation further comprises:
   about 0.01% to about 30% retinol,
   about 1% to about 80% ethoxydiglycol,
   about 10% to about 90% isopentyldiol,
   about 5% to about 90% dimethylisorbide, and
   about 8% to about 40% of the non-ionic surfactant,
      wherein the non-ionic surfactant is selected from polysorbate 80, polysorbate 20, or a combination thereof.

2. The method of claim 1, wherein the affected area is one or more of human skin, scalp, hair, and nails.

3. The method of claim 1, wherein the non-ionic surfactant is polysorbate 80.

4. The method of claim 1, wherein the formulation further comprises an antioxidant.

5. The method of claim 1, wherein the formulation further comprises bakuchiol.

6. The method of claim 1, wherein the method further comprises periodically repeating the application of the formulation.

7. The method of claim 1, wherein the method is administered once, twice, thrice or four times daily.

8. The method of claim 1, wherein the topical formulation further comprises:
   about 0.01% to about 10% caffeine;
   about 0.1% to about 15% green tea polyphenols isolated and purified from the leaves of *Camellia sinensis* plants;
   up to about 20% bakuchiol;
   up to about 20% black tea extract; and
   up to about 20% licorice root extract.

9. The method of claim 1, wherein the formulation is selected from the group consisting of a serum, an emulsion, a foam, a spray, an ointment, a gel and a lotion.

* * * * *